(12) United States Patent
Chung et al.

(10) Patent No.: US 7,386,347 B2
(45) Date of Patent: Jun. 10, 2008

(54) ELECTRIC STIMULATOR FOR ALPHA-WAVE DERIVATION

(75) Inventors: Jong-Pil Chung, 434, Gunduk 1-ri, Sunjang-myeon, Asan-si, Chungcheongnam-do 336-892, Asan-si (KR); Sung-Min Kang, Seoul (KR); Ye-Won Kim, Seoul (KR); Chong-Hyun Lee, Seoul (KR)

(73) Assignee: Jong-Pil Chung (KR)

( * ) Notice: Subject to any disclaimer, the term of this patent is extended or adjusted under 35 U.S.C. 154(b) by 261 days.

(21) Appl. No.: 10/519,291

(22) PCT Filed: Jun. 20, 2003

(86) PCT No.: PCT/KR03/01220

§ 371 (c)(1),
(2), (4) Date: Dec. 23, 2004

(87) PCT Pub. No.: WO04/000413

PCT Pub. Date: Dec. 31, 2003

(65) Prior Publication Data

US 2006/0064139 A1   Mar. 23, 2006

(30) Foreign Application Priority Data

Jun. 24, 2002   (KR) ................ 10-2002-0035305
Jun. 11, 2003   (KR) ................ 10-2003-0037632

(51) Int. Cl.
    *A61N 1/18*   (2006.01)
    *A61N 1/32*   (2006.01)
(52) U.S. Cl. ................ 607/45; 607/33; 607/62; 607/118; 607/148; 607/60

(58) Field of Classification Search .......... 607/1, 607/2, 37, 38, 60, 62, 118, 148, 156, 45; 600/554, 322, 347; 439/909
See application file for complete search history.

(56) References Cited

U.S. PATENT DOCUMENTS 4,112,923 A * 9/1978 Tomecek ............... 600/11

(Continued)

FOREIGN PATENT DOCUMENTS

JP   1989-175867   7/1989

(Continued)

OTHER PUBLICATIONS

Asamato, Shunji, et al., "Activation of the Satiety Center by Auricular Acupuncture Point Stimulation," Brain Research Bulletin, vol. 29, pp. 157-164, 1992.

(Continued)

*Primary Examiner*—Kennedy J. Schaetzle
*Assistant Examiner*—Natasha Patel
(74) *Attorney, Agent, or Firm*—Cantor Colburn LLP

(57) ABSTRACT

An electric stimulator for alpha-wave derivation is characterized in that frequency selected from a range of 1 Hz to 50 Hz, preferably, 7 Hz to 14 Hz, and an output voltage are applied to auricle of a patient's ears to derive alpha-waves, and that cycle and intensity of stimulation are varied depending upon body temperature and blood sugar. Prompt reaction may be obtained by directly applying the voltage to the ears, and the reaction may continue when stimulation is extended. In addition, it is suitable to treat various diseases having common cause due to stress or arousal reaction in the human body.

15 Claims, 16 Drawing Sheets

U.S. PATENT DOCUMENTS

| | | | |
|---|---|---|---|
| 4,966,164 A | * | 10/1990 | Colsen et al. ................. 607/72 |
| 6,522,929 B2 | * | 2/2003 | Swing ......................... 607/50 |
| 6,553,263 B1 | * | 4/2003 | Meadows et al. ............. 607/61 |
| 6,662,051 B1 | * | 12/2003 | Eraker et al. ................. 607/59 |
| 6,662,052 B1 | * | 12/2003 | Sarwal et al. ................. 607/59 |

FOREIGN PATENT DOCUMENTS

| | | |
|---|---|---|
| JP | 1989-085336 | 4/1998 |
| JP | 1998-282983 | 10/1998 |
| JP | 2001-190637 | 7/2001 |
| KR | 10-2000-0074582 A | 12/2000 |
| KR | 10-2001-0094469 A | 11/2001 |
| KR | 20-2001-0002365 | 12/2001 |

OTHER PUBLICATIONS

Schachter, Steven C., et al., "Vagus Nerve Stimulation," Epilepsia, vol. 39, No. 7, pp. 677-686, 1998.

Korean Intellectual Property Office, International Search Report, Date of Mailing: Mar. 15, 2004.

* cited by examiner

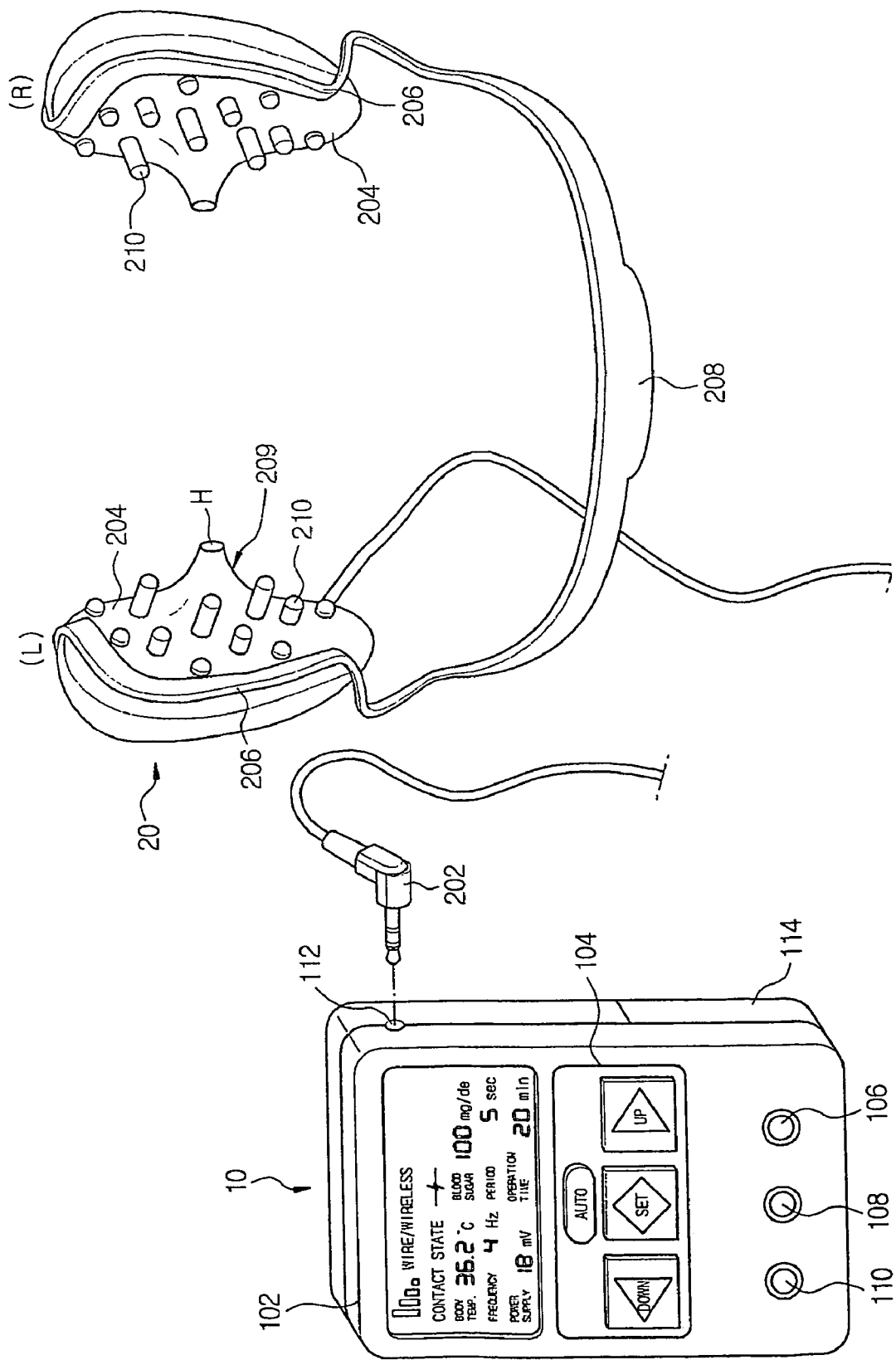
[FIG 1]

[FIG 2]
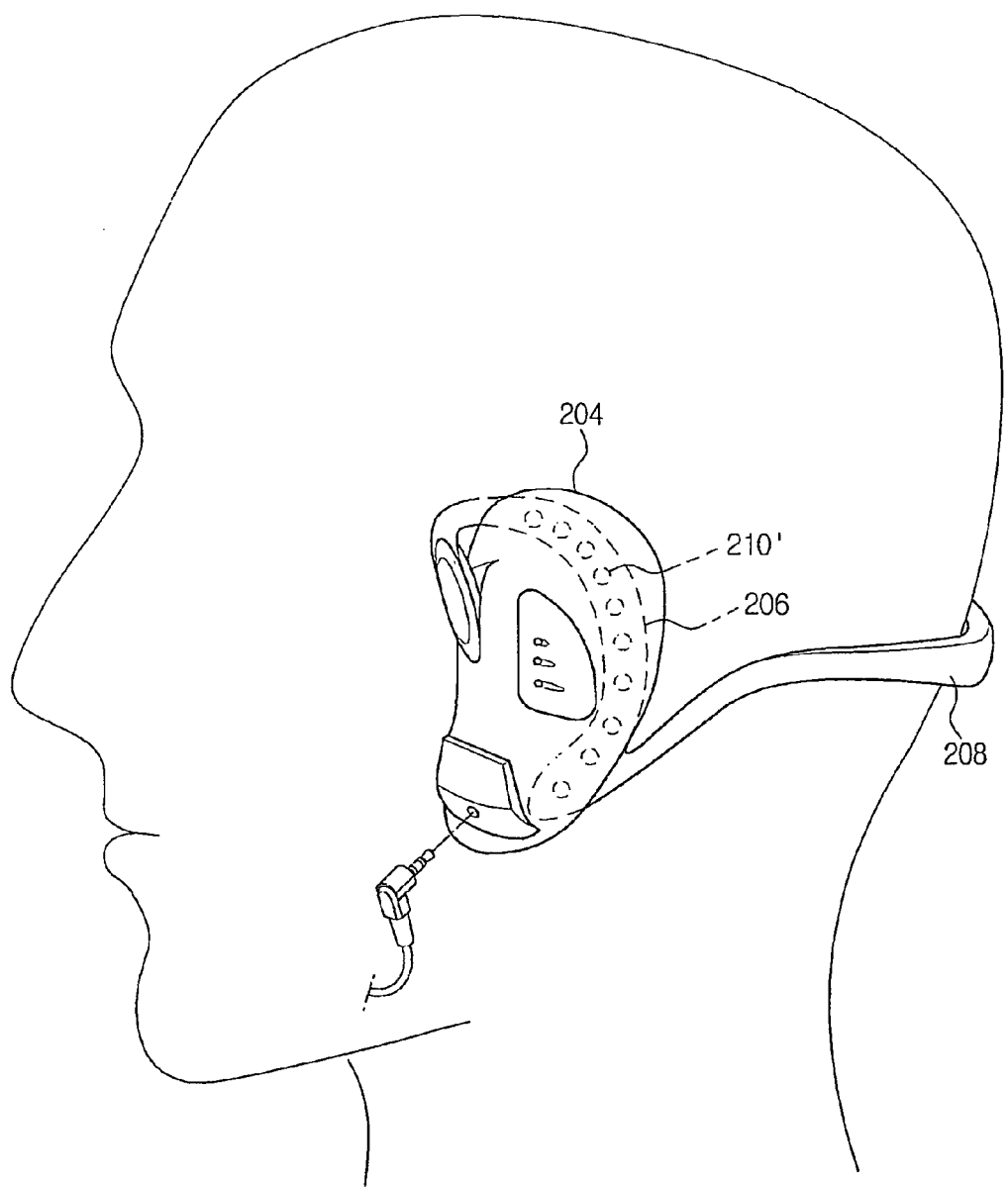

[FIG 3]
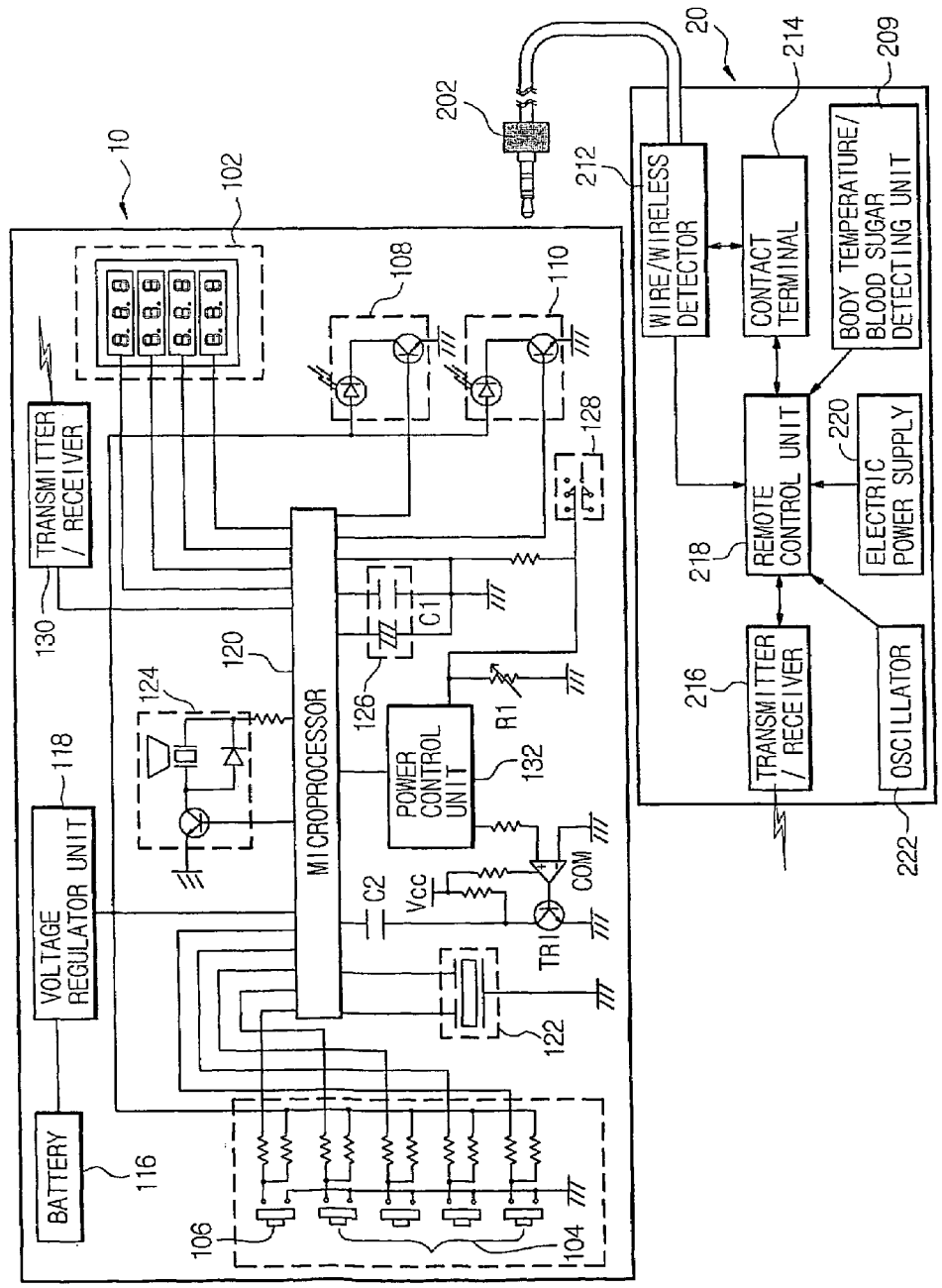

[FIG 4]
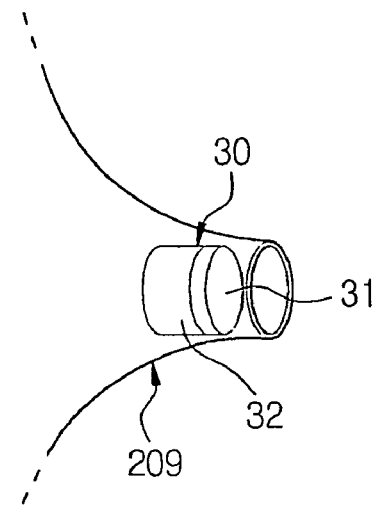
[FIG 5A]
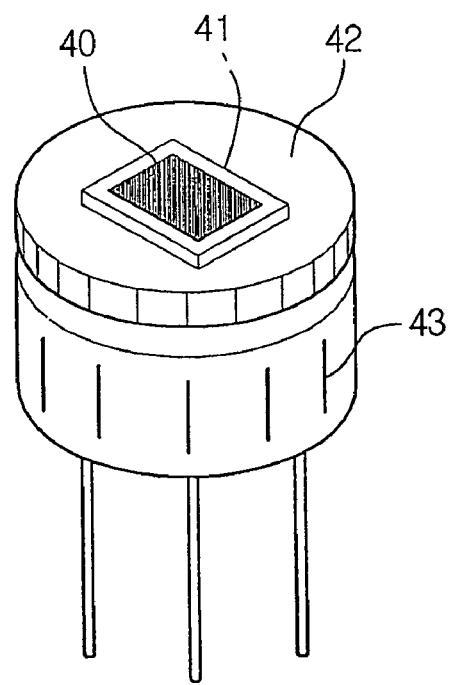

[FIG 5B]
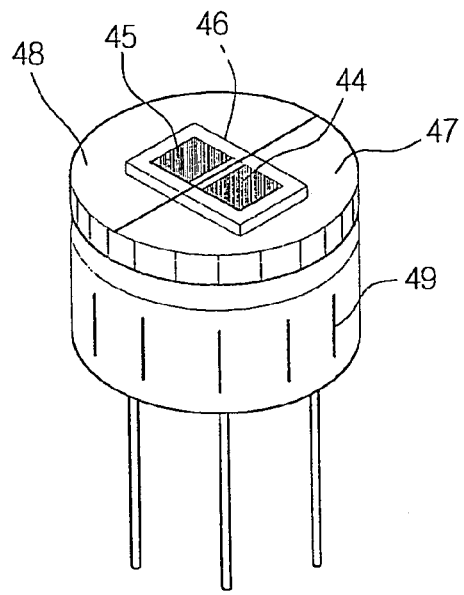
[FIG 6A]
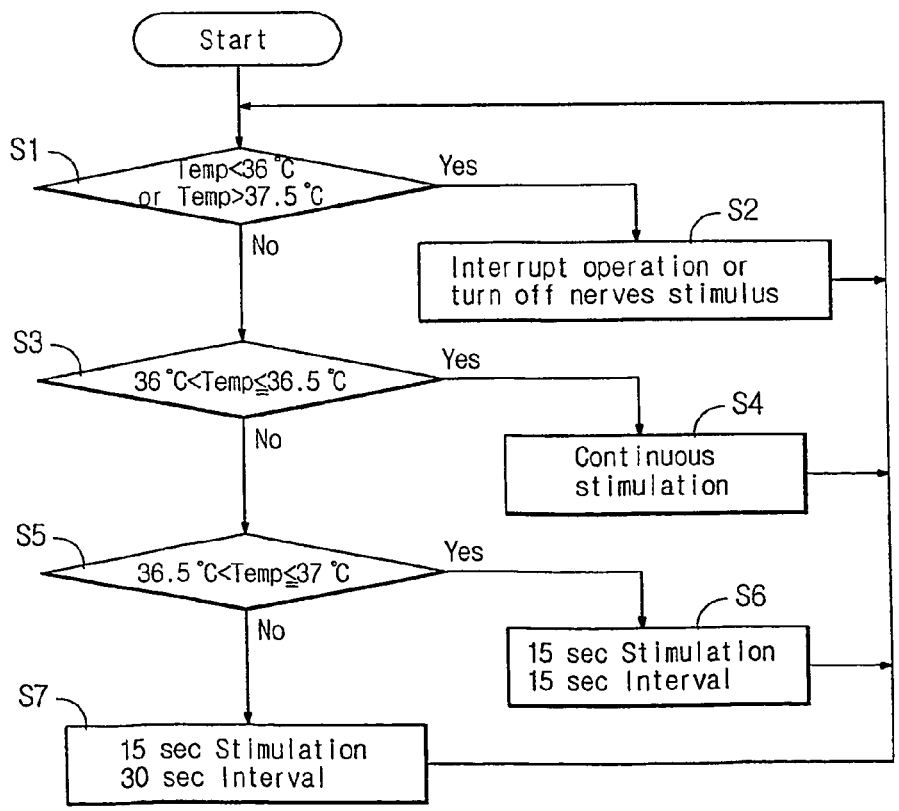

[FIG 6B]
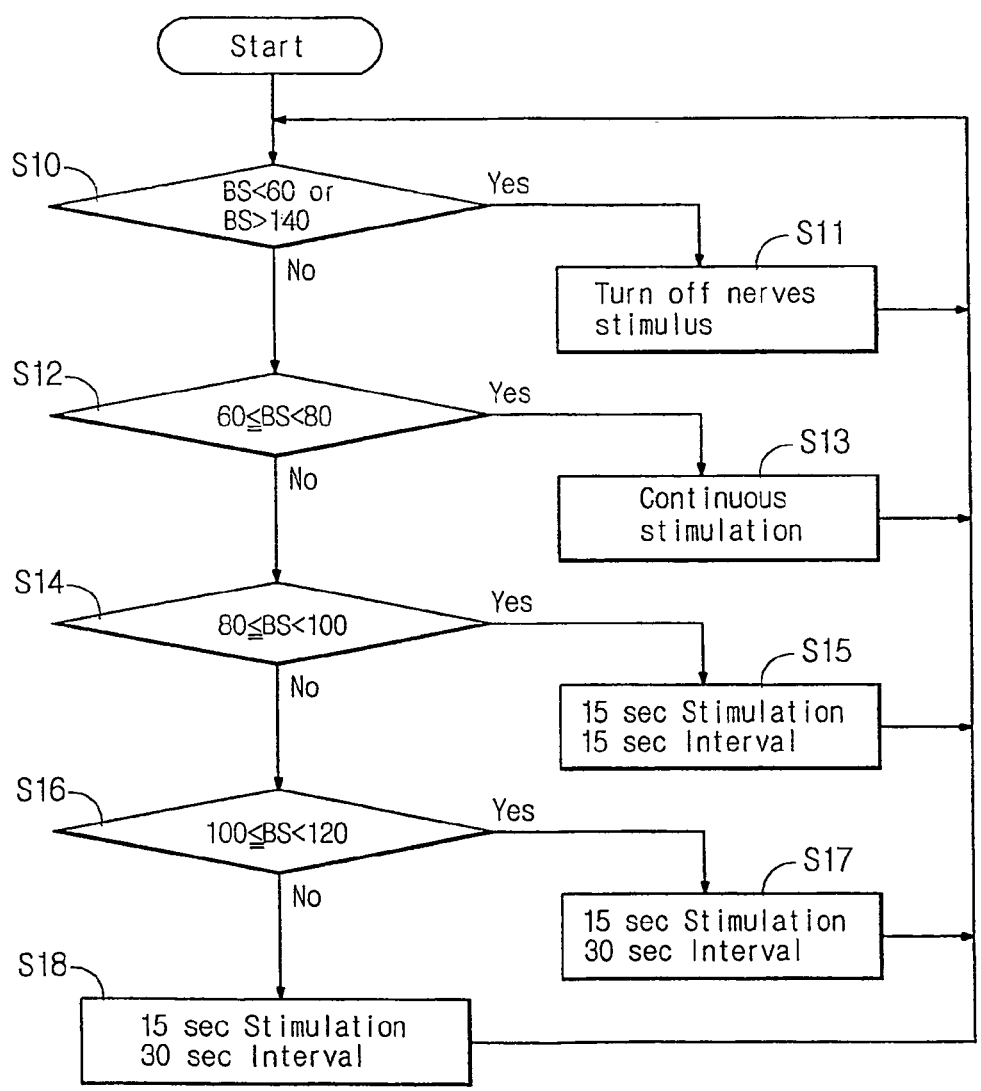

[FIG 6C]
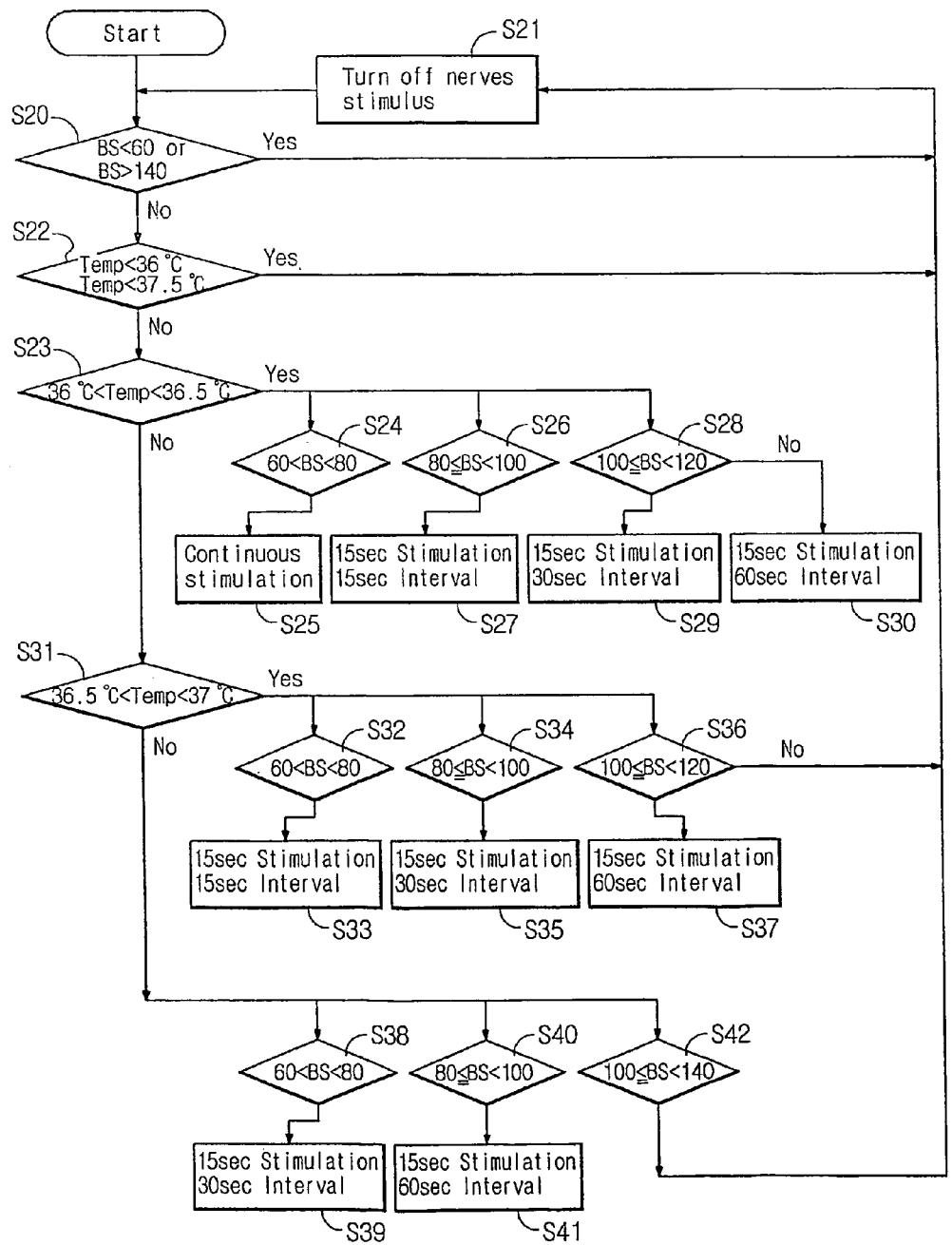

[FIG 7A]
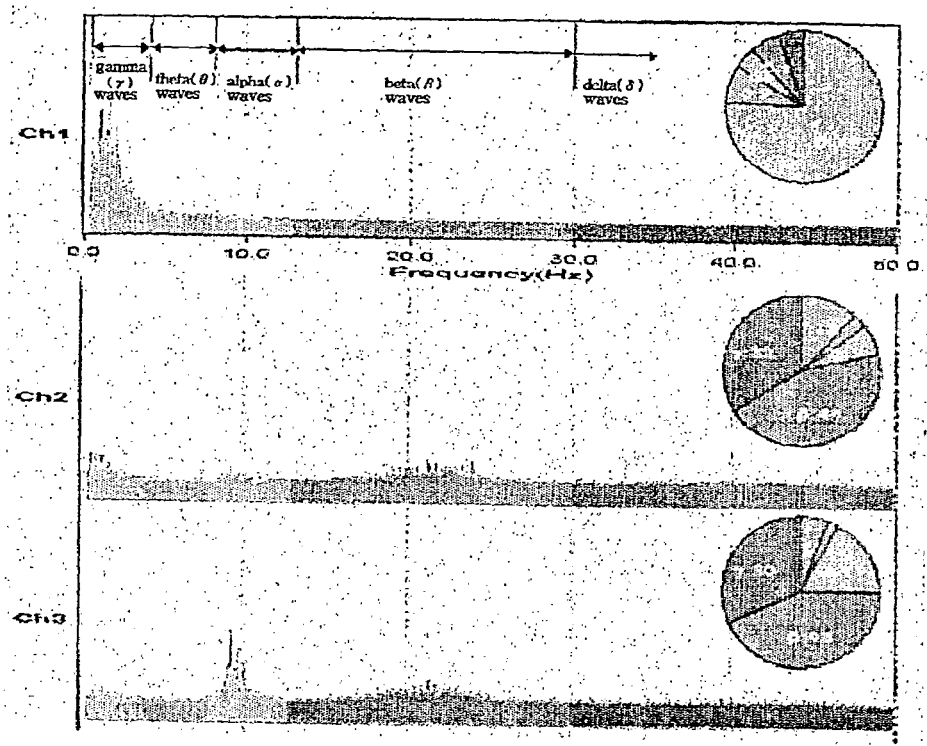
[FIG 7B]
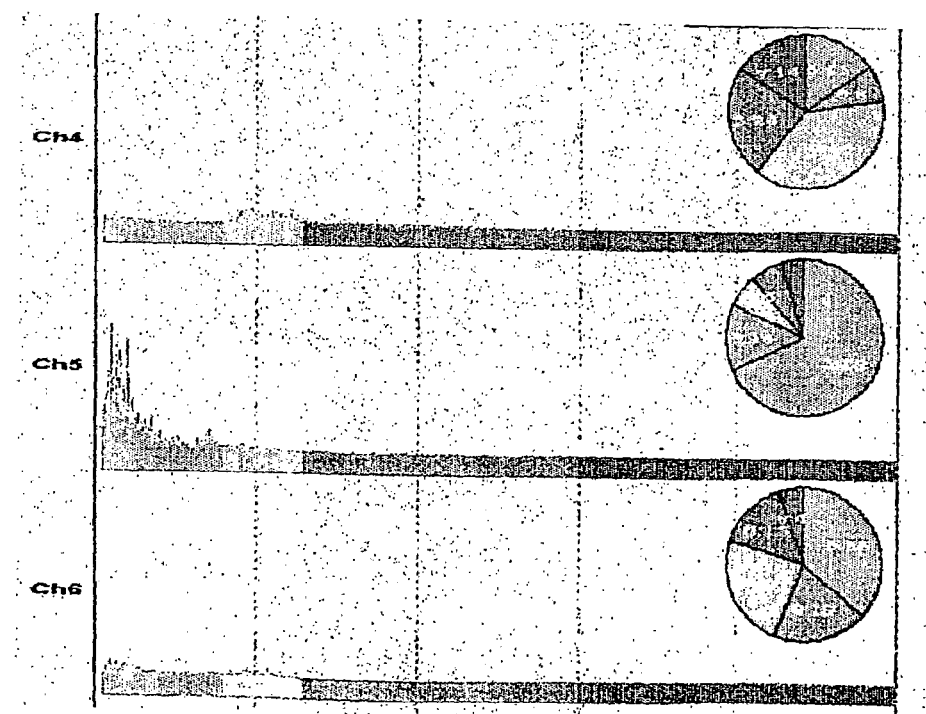

[FIG 7C]
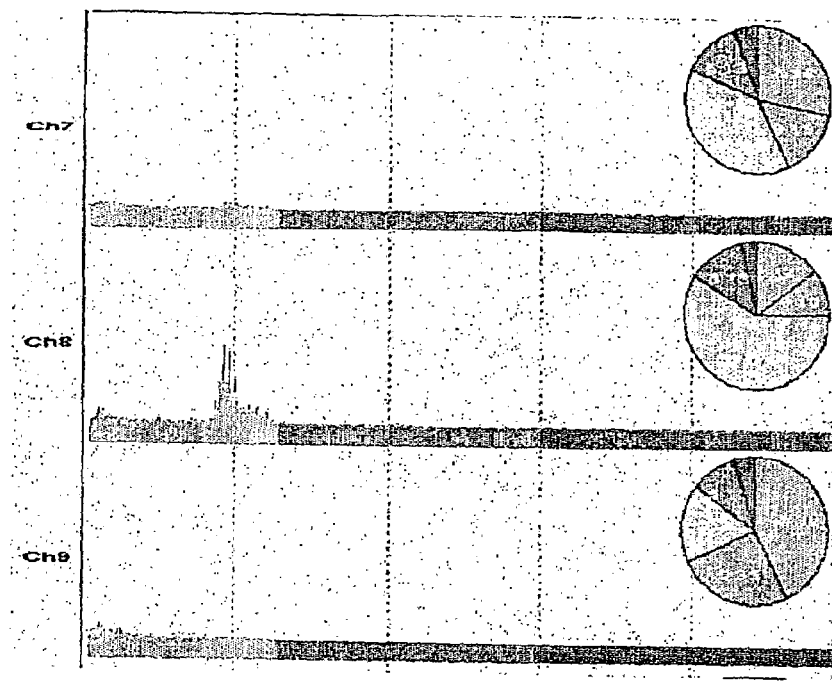
[FIG 7D]
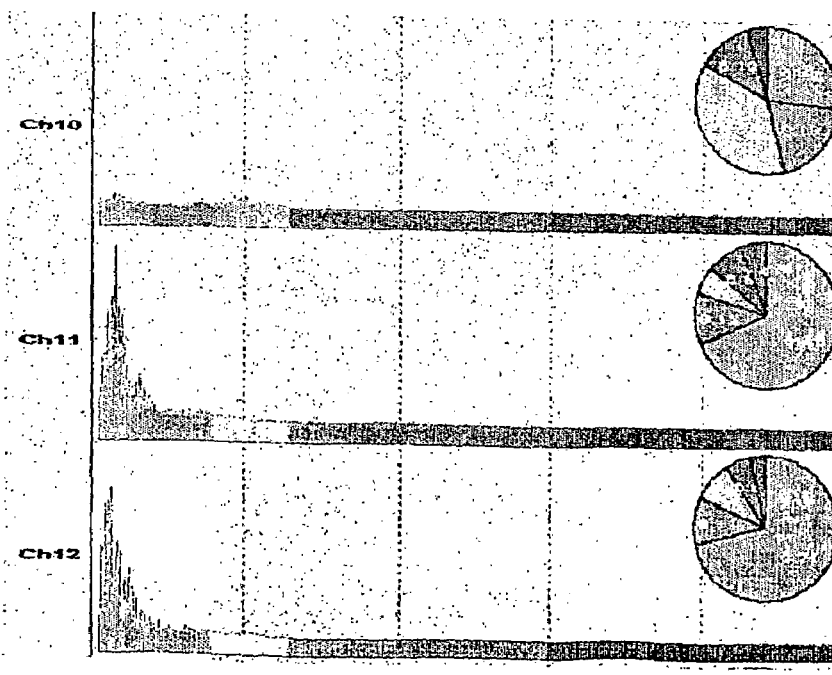

[FIG 7E]
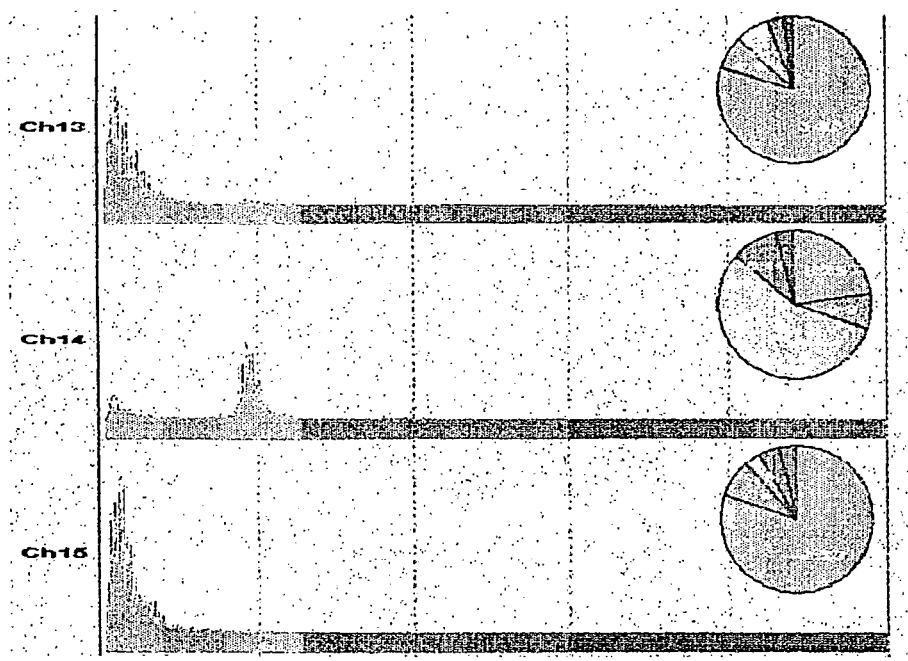
[FIG 7F]
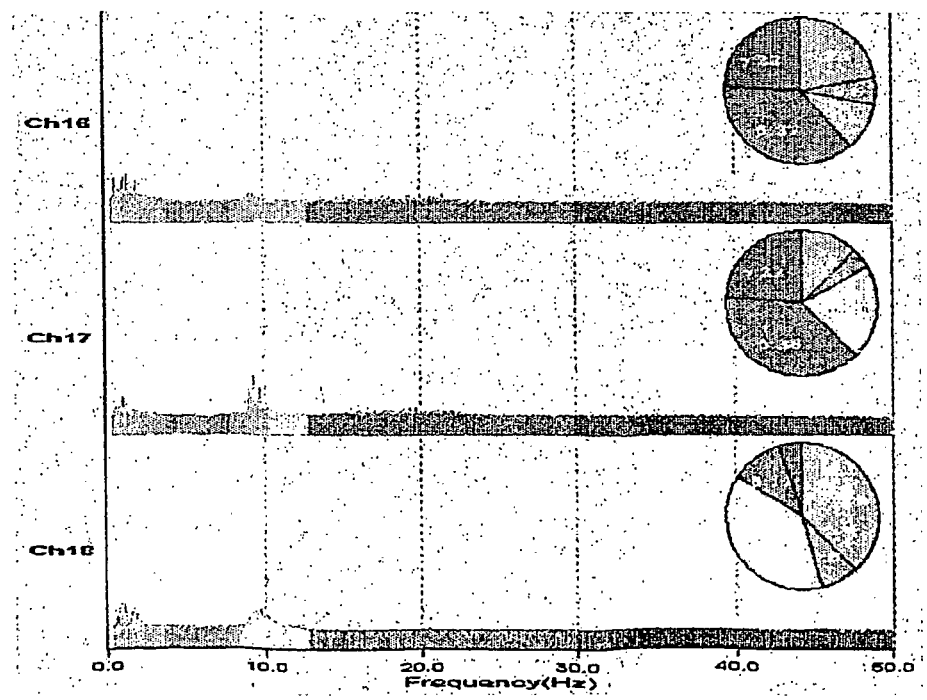

[FIG 8A]
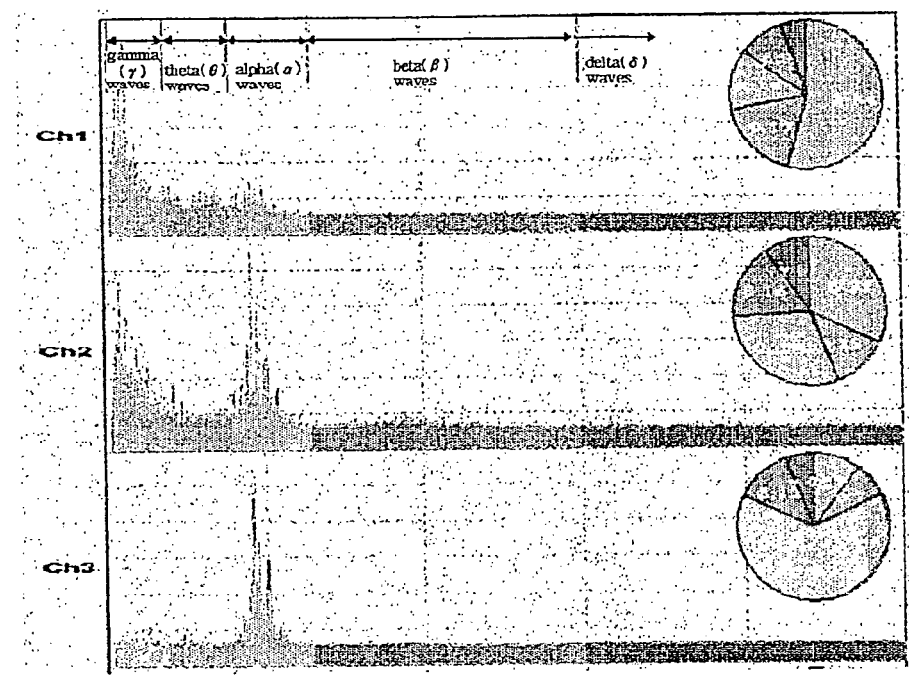
[FIG 8B]
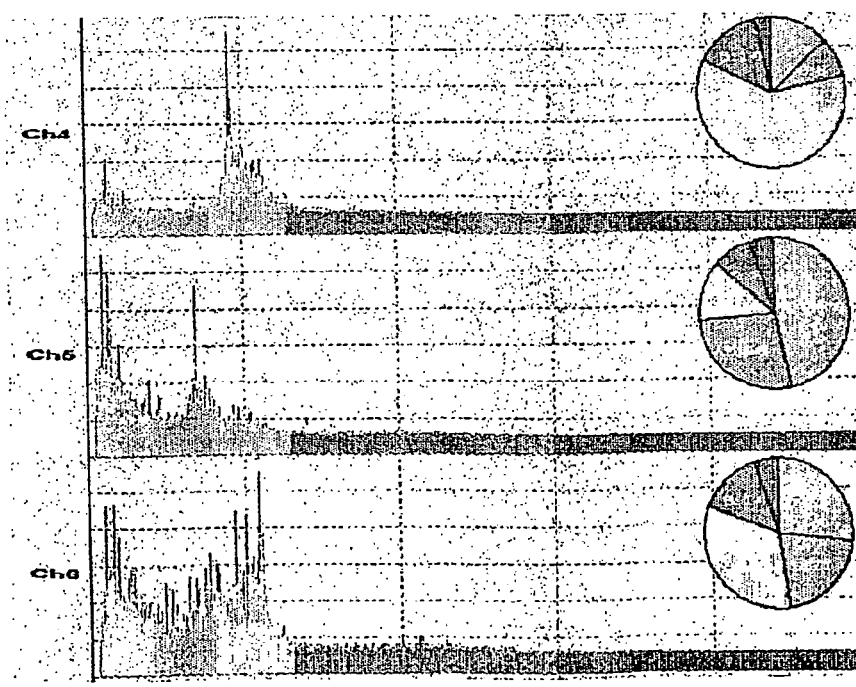

[FIG 8C]
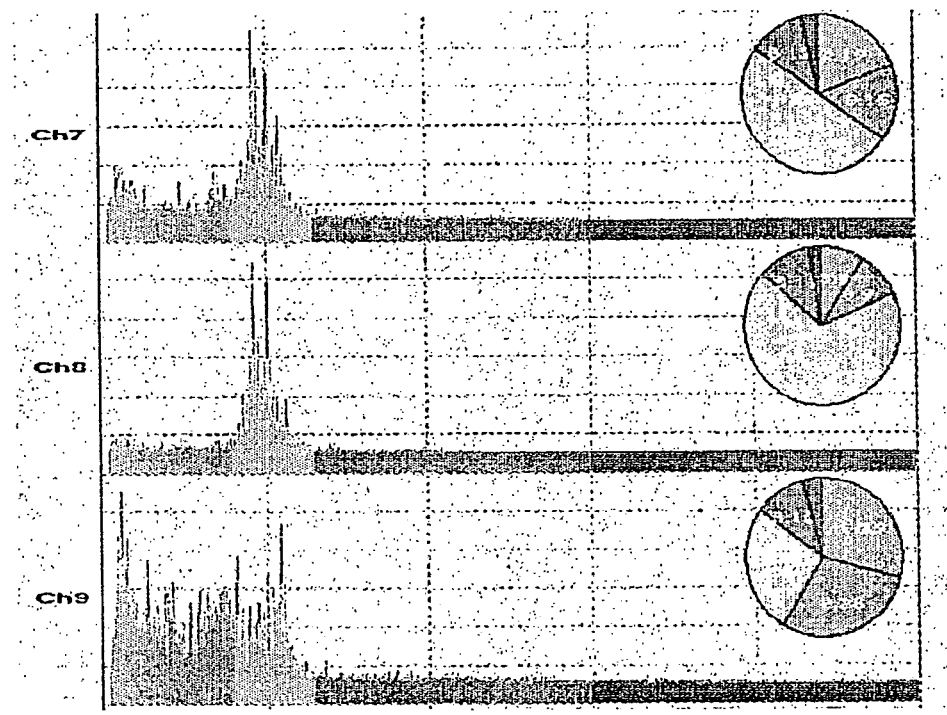
[FIG 8D]
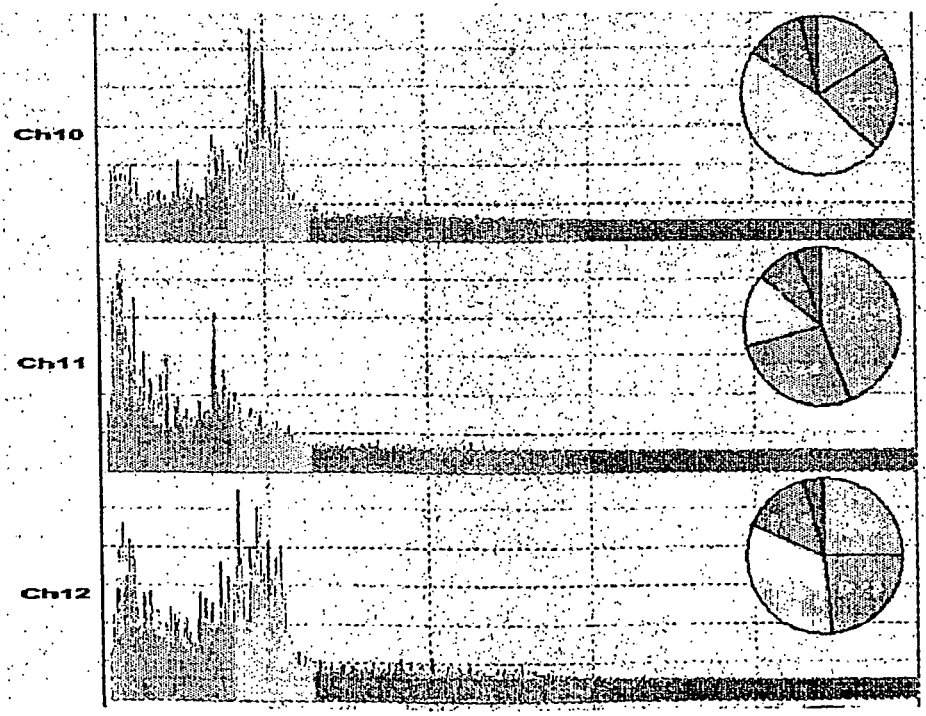

[FIG 8E]
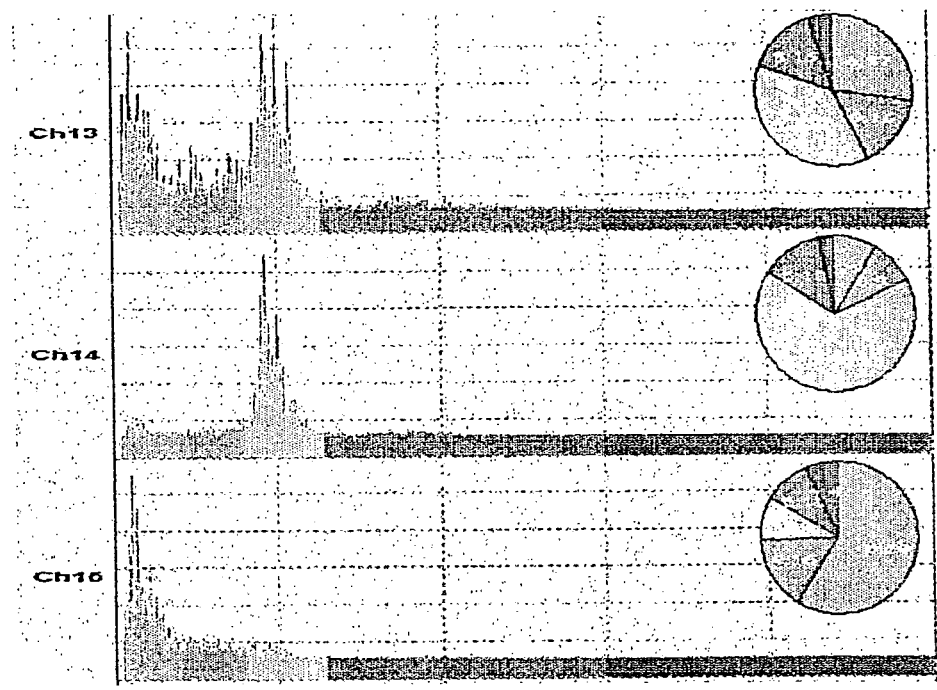
[FIG 8F]
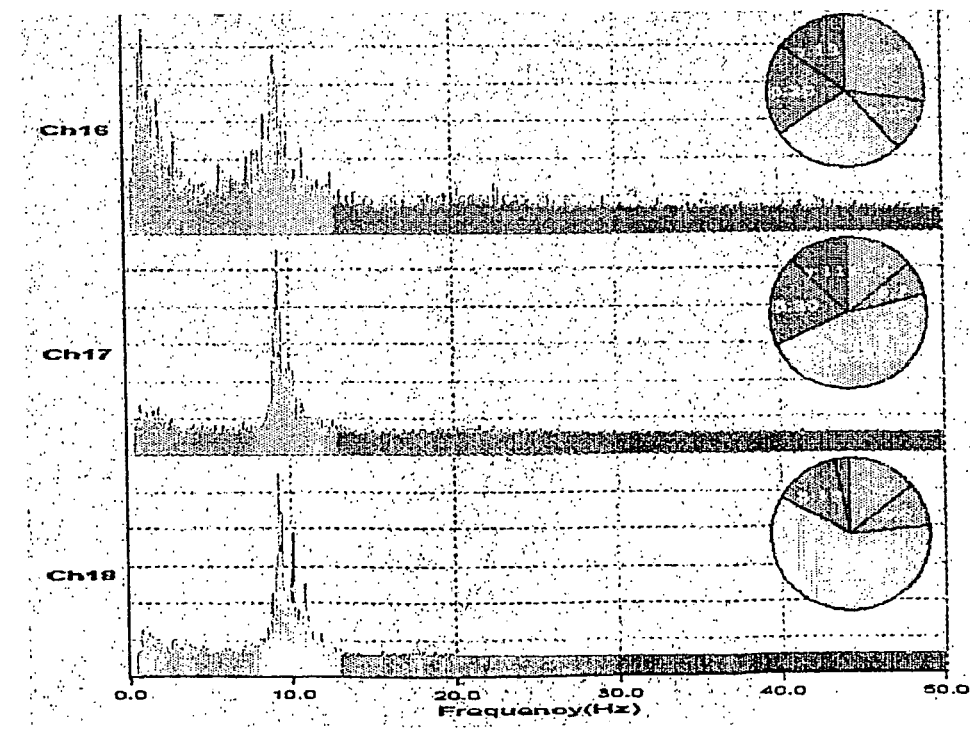

[FIG 9A]
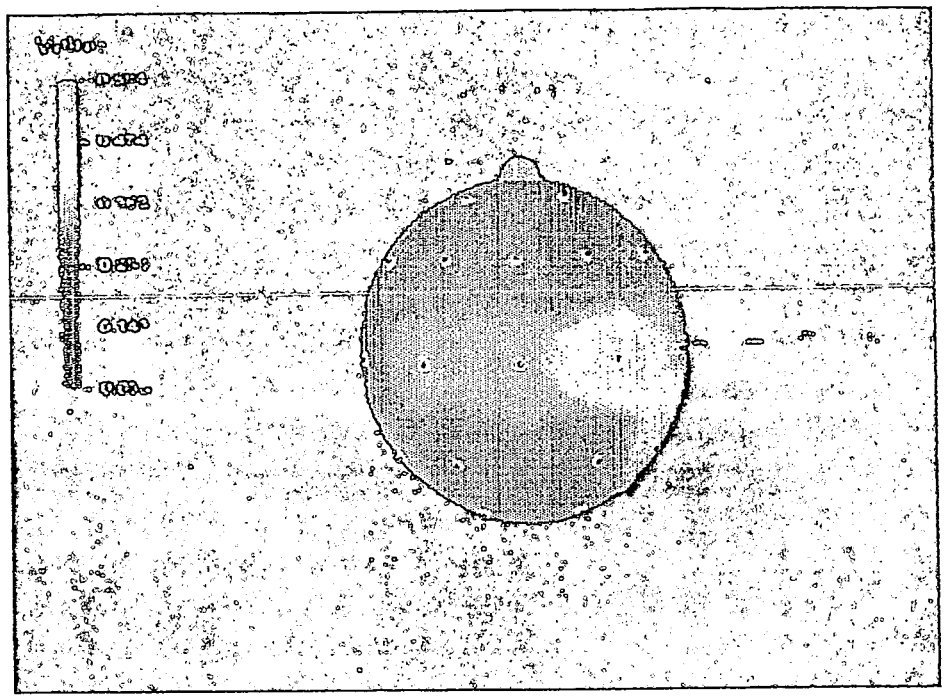
[FIG 9B]
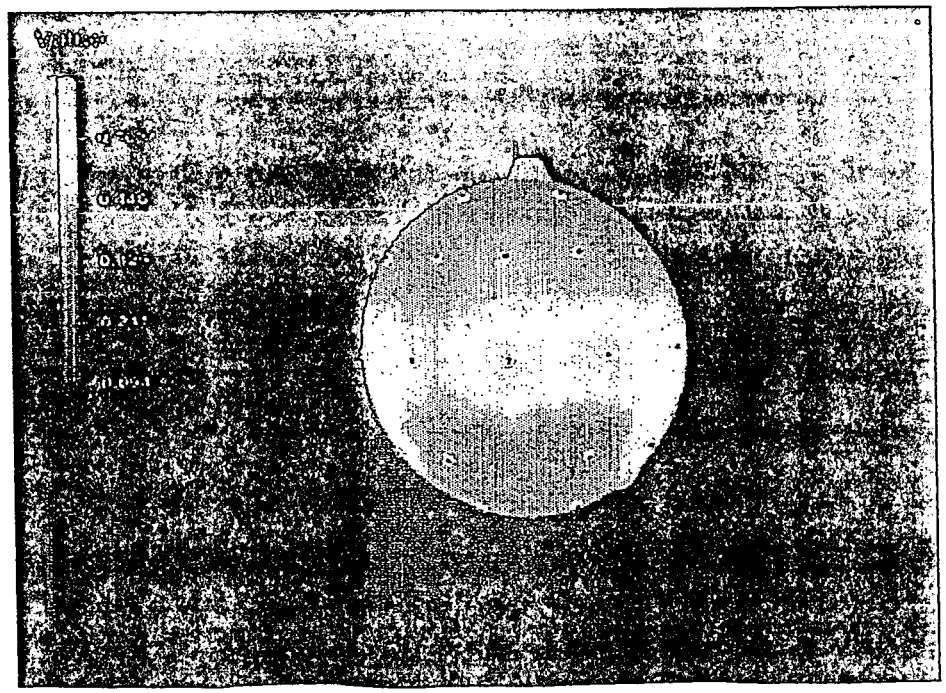

[FIG 10A]
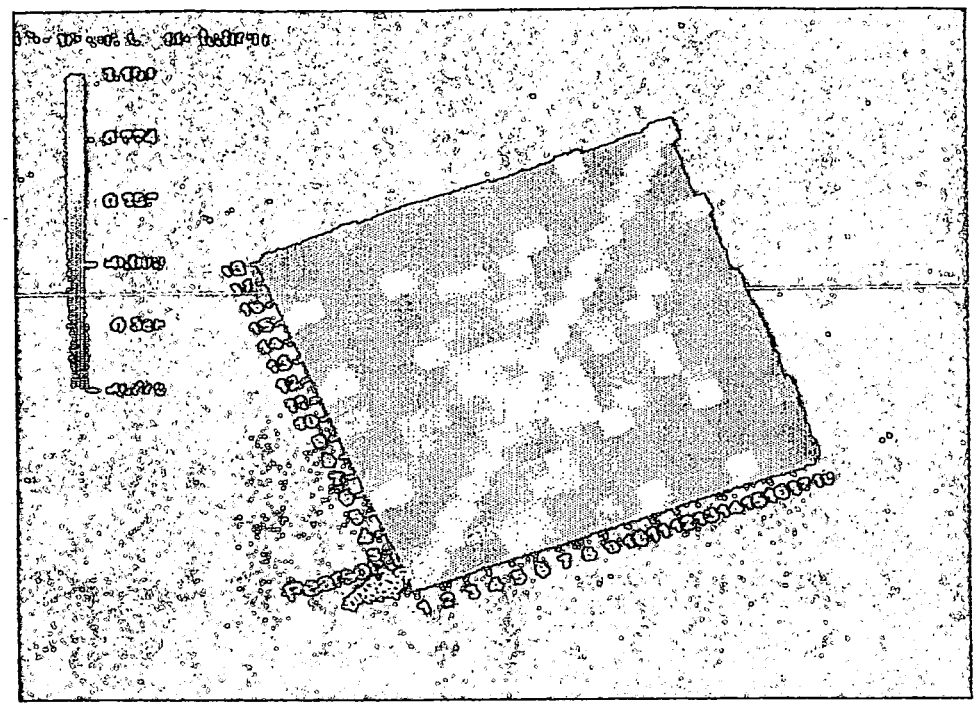
[FIG 10B]
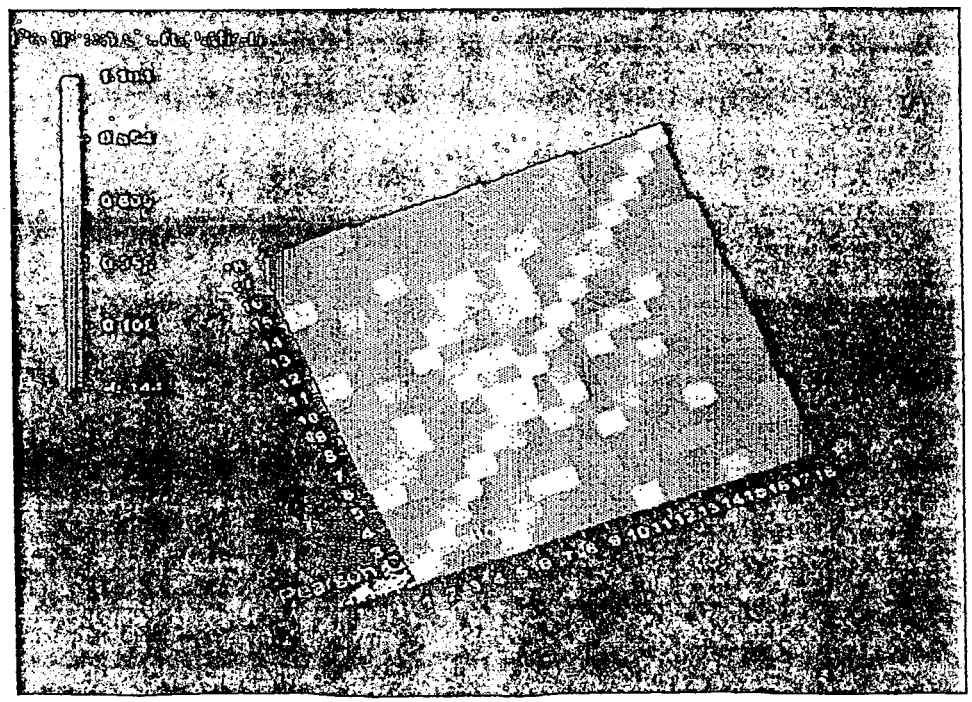

[FIG 11A]
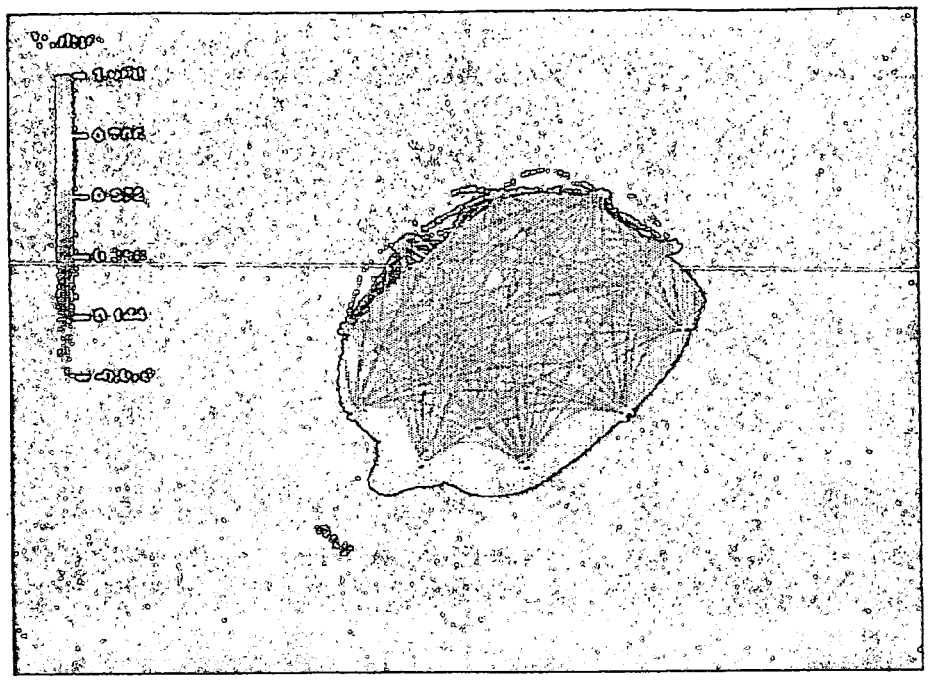
[FIG 11B]
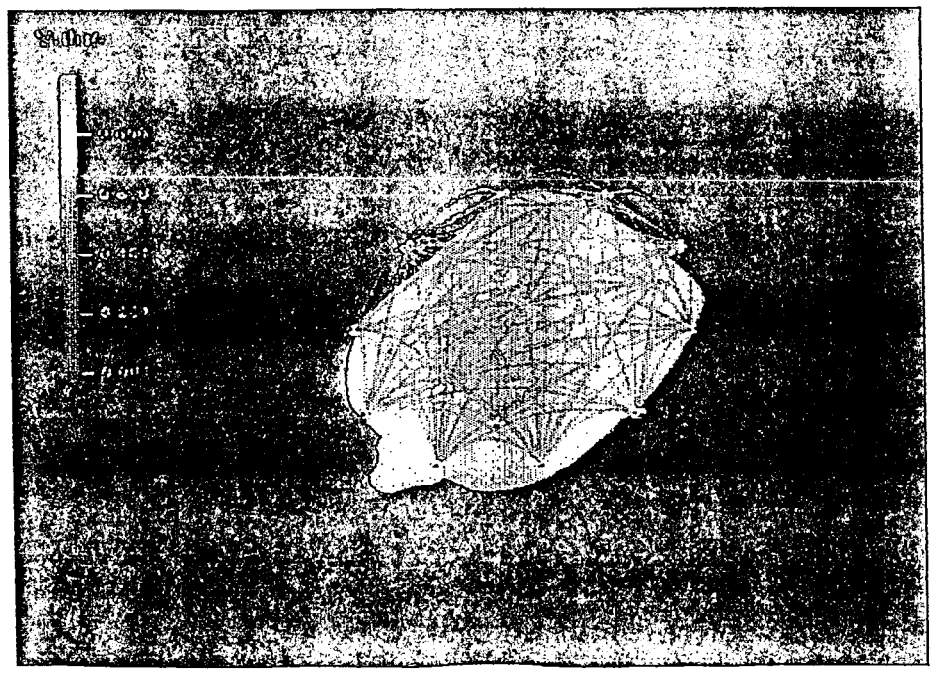

ELECTRIC STIMILATOR FOR ALPHA-WAVE DERIVATION

TECHNICAL FIELD

The present invention relates to an electric stimulator for alpha-wave derivation, and more particularly, to an electric stimulator for alpha-wave derivation which applies electric stimulation to auricle of vagus nerves of an ear to derive an alpha-wave in a brain wave, thereby performing an effective medical treatment for various disorders.

BACKGROUND ART

Recently, an electric stimulator for vagus nerves can now be used for treating epilepsy and hypochondria with FDA approval to the cervix. In addition, it was reported that the electric stimulator is effective for treatment of obesity in epileptics. According to the electric stimulating therapy for cervix of vagus nerves, the vagus nerves serve as transferring paths, which transfer arousal information of lower organs to the cerebrum. Since the vagus nerves are frequency dependent, a difference that induces synchronous waves and asynchronous waves in brain waves were discovered (see "Vagus Nerve Stimulation" by Steven C. Schachter and Clifford B. Saper: Epilepsia 39: 682, 1998).

Relating to the treatment by use of stimulation of the cervix of vagus nerves, it was reported in oriental medicine that obesity, pains and internal organ diseases could be treated by acupuncture to both ears. Since a theoretical basis of oriental medicine is based upon a therapy using energy and meridians, the ear acupuncture therapy overlooks a role of stimulus conduction via nerves. Therefore, oriental medicine does not present a fundamental method of accurate treatment.

A region (meridian) in which acupuncture is to be performed for treating obesity, pains and internal organ diseases in oriental medicine corresponds to a region in charge of conducting stimulus via the cervix of vagus nerves. Meanwhile, it was reported in western medicine that electric stimulation therapy using the cervix of vagus nerves to treat epilepsy or hypochondria has a remarkable effect in obesity treatment (see "Activation of the Satiety Center by Auricular Acupuncture Point Stimulation" by Asamoto S and Takeshige C: Brain Res Bull 29(2): 157-164, August 1992). Electric stimulators for applying electric stimulation to both ears have been proposed in Japan (1994 and 2001), in which the stimulators are to stimulate the region (meridian) known as an obesity treating point in oriental medicine. However, the stimulators are not utilized as an alpha-wave generating apparatus, which can obtain effects of psychological stability and treatment of various diseases by suppressing stress reaction of a human body. The reason why its object is different from each other is that the electric stimulating frequency and its intensity for generating alpha-waves are remarkably different from each other.

Recently, the electric stimulation therapy using the cervix of vagus nerves is performed by removing wanted skin to expose the cervix of vagus nerves, winding a coil around the cervix, and grafting a microchip therein. However, operation costs are very expensive, and the region must be again operated on every few years in order to replace the battery. In addition, a permanent scar is left due to the incision, and a patient's heart is at risk as a result of the operation. Furthermore, the patient is under a lot of mental stress due to operation.

Meanwhile, according to oriental medicine of performing acupuncture to the ear, although treatment effect for obesity, pains and internal organs diseases are substantially regarded as treatment effect due to stimulation of the vagus nerves, it places special stress on energy and meridians, thereby disregarding the effect of stimulation via nerves. Accordingly, since oriental medicine does not know acknowledgingly that the simulation conducting effect of the vagus nerves is differently derived depending upon the frequency by electrical synapse of the vagus nerves, effective treatment is not performed. In addition, a patient must go to hospital every day so that acupuncture may be performed. Since a chronic disease results from the reduction or blunting of regulation of vagus nerves, a patient's symptoms relapse when acupuncture is not performed. Therefore, a patient's life is encumbered, because of frequent visits to hospital throughout the patient's life (see "Dynamics of Obesity" by Sun-Hyen Shin; Clinical Obesity $2^{nd}$ Edition, 27, 2001).

Recently, some methods for deriving alpha-waves have been proposed: one is to derive synchronization of brain waves of the central nervous system by radiating light and sound having a constant cycle to eyes and ears (for example, Mcsquare™); and the other is to derive synchronization of brain waves by directly radiating a magnetic field from the exterior of skull to the interior thereof (for example, Solomon™). Although stimulation is derived during a long period of time, the synchronization deriving effect can be obtained after only a short period of time. The above methods do not directly but indirectly derive the brain waves by indirect transmission of stimulation to the cerebral cell. The effect does not promptly happen; and the reaction does not continue when stimulation is extended. Accordingly, it is not suitable to treat various diseases having common cause due to stress or arousal reaction in the human body by such methods.

DISCLOSURE OF THE INVENTION

Therefore, an object of the present invention is to solve the above problems and to provide an electric stimulator for alpha-wave derivation capable of implementing the following functions:

1. The alpha-wave is derived by selecting auricles of both ears in which only the auricle among vagus nerves known as one having a part in synchronization of brain waves is positioned near to the skin, and by effectively implementing the stimulation of a specific frequency and intensity to treat various chronic diseases that result from reduction or blunting of regulation of vagus nerves, thereby maximizing the treating effect of the disease;

2. Dimensions of the electric stimulator are minimized to reduce the inconvenience of daily treatment of attaching the stimulator to a body, thereby periodically and continuously deriving alpha-waves and thus maximizing the effect of treatment;

3. Cymba conchae (100%), which is a prominent region of vagus nerves, and a front surface (50%) and rear surface (50%) of auricle concha may be simultaneously stimulated, and the effect of treatment may be kept without causing a patient inconvenience in daily life such as walking or exercise. In order to accomplish the above effects, a unit for detecting the detachment of a stimulating pad from a stimulating point of the patient is provided, or a unit is designed so that the detachment or noticeability of others is reduced;

4. In order to minimize wearing sensitivity, the electric stimulating apparatus of low electric power consumption is developed as a circuit of a digital mode. With this development, the intensity and cycle of the stimulating signal may conveniently be adjusted by the patient;

5. Being different from a conventional alpha-wave deriving unit, the stimulator according to the present invention includes a transmitter and a receiver that are separately divided, thereby minimizing the dimensions of the stimulator. The stimulator may be continuously attached to the body to continuously derive alpha-waves, and it cannot be easily noticed by others; and 6. Considering conditions of the patient at use, i.e., humidity and contacting state of a surface to be attached, stimulation is controlled, and also stimulation is controlled according to monitored body temperature and/or blood sugar.

To accomplish these objects, there is provided an electric stimulator for alpha-wave derivation comprising: a low frequency generating circuit for generating an output voltage of frequency and cycle selected from a range of 1 Hz to 50 Hz to derive alpha-waves; and a contacting portion for applying a current to an auricle of vagus nerves of an ear. Preferably, the low frequency generating circuit generates an output voltage of frequency and cycle selected from a range of 7 Hz to 14 Hz.

According to another aspect of the present invention, there is provided an electric stimulator for alpha-wave derivation comprising: a control section including: a key input unit for supporting user operation; a microprocessor for setting a frequency, a voltage, a cycle and an operation time according to the a key input signal transferred from the key input unit, for controlling an output of the frequency and voltage according to the set, for determining whether the outputted frequency and voltage are applied to an ear of a user, for performing a switching of a wire/wireless mode by determining whether a jack is connected to an electric stimulating unit, for outputting a transmitting signal to wirelessly transmit setting data after a predetermined time, when the wireless mode is switched, and for outputting a turn-on/off signal corresponding to an alarm signal and the turn-on/off signal indicative of a wire/wireless mode control state; a control-side transmitter/receiver for transmitting the setting data according to the transmitting signal and transmitting/receiving input/output data; an oscillator for oscillating at a frequency of 1 Hz to 50 Hz according to a frequency output control; and a connector connected to the jack and connected to the microprocessor for determining the wire/wireless state according to variations of input current value; a connecting line connecting the connector with the jack and transferring the frequency and voltage from the jack to the electric stimulating unit; and the electric stimulating unit including: a contacting terminal connected to the connecting line and contacted to an auricle of vagus nerves of the ear; a wire/wireless detecting unit interposed between the connecting line and the contacting terminal for detecting the wire/wireless mode state according to whether it is connected to the jack or not; a remote control unit for determining the wire/wireless mode state, for controlling operation of the electric stimulating unit itself, in case of the wireless mode, and for controlling the frequency and voltage according to the set data transmitted from the control-side transmitter/receiver; a transmitter/receiver communicating with the control-side transmitter/receiver for transmitting the input/output data to the remote control unit; an oscillator for supplying the frequency to the remote control unit; and a battery for supplying an electric power to the remote control unit.

Preferably, the oscillator oscillates at 7 Hz to 14 Hz. The electric stimulator further comprises a non-contact detector for detecting whether the electric stimulating unit is non-contacted to the ear by use of charge accumulation flowing through the jack of the control unit to output the result to the microprocessor. The microprocessor further includes an A/D converter and a D/A converter for converting the signal inputted/outputted to/from the electric stimulating unit. The microprocessor further includes a timer operating according to a setting data comprising a cycle and operation time.

The connecting line has a jack at both ends of the connecting line, wherein the jack is detached to the connector and electric stimulating unit. The electric stimulator further comprises an alarm for outputting an alerting sound, when an alarm signal is outputted according to the determining result of voltage application to the ear. The electric stimulator further comprises a display for displaying a set value according to a key input signal transmitted from the key input unit, and for outputting or lighting an operation state.

In order to prevent an electric short circuit when the contact state based on the signal transmitted from the non-contact detecting unit is determined, the electric stimulator further comprises; a variable resistor R1 forming a closed circuit together with the contact terminal for performing a voltage drop according to a resultant resistance value; a voltage comparator COM for comparing a voltage generated by the resultant resistance value with a predetermined reference voltage; a switch TR1 switched according to the comparison results of the voltage comparator COM; a capacitor C2 discharged by the switch TR1 to transmit a signal notifying whether normality or not to the microprocessor; and an electric power control unit, which it determines as the normality when the capacitor C2 is discharged, and interrupts supply of a direct current, and which only the voltage drop happens by the variable resistance R1 when the capacitor C2 is not discharged.

The electric stimulating unit has a body temperature detecting unit made in a shape like a crater of a gently slant ridgeline to be easily inserted in an external auditory meatus, so as to detect a signal for determining body temperature using an infrared processing module, and the body temperature detecting unit has a drilled top surface H to receive an infrared signal. The electric stimulating unit has a blood sugar detecting unit made in a shape like a crater of a gently slant ridgeline to be easily inserted in an external auditory meatus, so as to detect a signal for determining blood sugar using an infrared processing module, and the body temperature detecting unit has a drilled top surface H to receive an infrared signal. The electric stimulating unit has a body temperature/blood sugar detecting unit made in a shape like a crater of a gently slant ridgeline to be easily inserted in an external auditory meatus, so as to detect a signal for determining body temperature and blood sugar using an infrared processing module, and the body temperature detecting unit has a drilled top surface H to receive an infrared signal. Alternatively, the infrared processing module includes a filtering portion and an infrared detecting portion, in which a sensing region is enclosed by a silicon window having a long pass filter, through which only infrared radiation emitted from the external auditory meatus is passed, and which a front of the sensing region is enclosed by a proper infrared bandpass filter having a spectrum characteristic to a radiation line of a measured analyte.

BRIEF DESCRIPTION OF THE DRAWINGS

FIG. 1 is a perspective view illustrating the construction of an electric stimulator for an alpha-wave derivation according to the present invention.

FIG. 2 is a view depicting a state of use of an electric stimulating headphone.

FIG. 3 is a schematic view depicting a control box of an electric stimulator for alpha-wave derivation according to one preferred embodiment of the present invention.

FIG. 4 is a perspective view depicting the construction of an infrared processing module.

FIGS. 5a and 5b are perspective views depicting the construction of an infrared processing module.

FIGS. 6a to 6c are flowcharts depicting a stimulating method according to body temperature and/or blood sugar.

FIGS. 7a to 7f are graphs quantitatively showing distribution of alpha waves, beta waves, gamma waves and theta waves before using an electric stimulator for alpha-wave derivation according to the present invention.

FIGS. 8a to 8f are graphs quantitatively showing distribution of alpha waves, beta waves, gamma waves and theta waves after use of an electric stimulator for alpha-wave derivation according to the present invention.

FIGS. 9a and 9b are views illustrating the state which alpha power is increased in a head before and after use of an electric stimulator for alpha-wave derivation according to the present invention.

FIGS. 10a and 10b and FIGS. 11a and 11b are views illustrating the state which synchronization is increased in a forebrain before and after use of an electric stimulator for alpha-wave derivation according to the present invention.

BEST MODE FOR CARRYING OUT THE INVENTION

Reference will now be made in detail to preferred embodiments of the present invention as illustrated in the accompanying drawings.

FIG. 1 is a perspective view illustrating the construction of an electric stimulator for an alpha-wave derivation according to the present invention. FIG. 2 is a view depicting a state of use of an electric stimulating headphone. Referring to FIGS. 1 and 2, the electric stimulator for alpha-wave derivation mainly includes a control box 10 and an electric stimulating headphone 20.

The control box 10 is provided at a front thereof with a display 102, setting keys 104, a power input button 106, a wire/wireless mode indicating lamp 108, and a touch state indicating lamp 110. The display 102 displays a contact state, body temperature, and blood sugar, as well as frequency, voltage, period, operating time and the like, which are set by the user. Also, the display 102 displays a residual amount of an electric power and wire/wireless mod. The setting keys consist of a mode select key SET, up/down control keys UP and DOWN, and an auto-mode key AUTO. The control box 19 is provided at one side thereof with a connecting terminal 112 connected to a jack 202 of the electric stimulating headphone 20. A battery case 114 is mounted to a rear lower end of the control box 10 to accommodate a battery.

The electric stimulating headphone 20 is provided as a headphone shape in the embodiment. The electric stimulating headphone 20 includes left and right stimulating member L and R each having a front stimulating portion 204 and a rear stimulating portion 206 to effectively apply the electric stimulation to user's ears. The left stimulating member L is connected to the right stimulating member R via a connecting band 208. The front stimulating portion 204 is formed in an ear shape so as to selectively apply the electric stimulation to any a front side of the ear. The rear stimulating portion 206 is formed in a shape to enclose a rear side of the ear so as to effectively apply the electric stimulation to the rear side of the ear. The electric stimulating headphone 20 is an example of the present invention, but the present invention may be formed in an acousticon shape for stimulating cymba conchae and a front surface of auricle concha, an earphone shape for stimulating the front surface of the auricle concha, a spectacular's leg stimulator shape for stimulating a rear surface of the auricle concha, a decoration shape which is not distinguishable from general earrings, a connector for stimulators at both front and rear surfaces of the auricle concha, or the like, so as to stimulate the front surface (50%) of the auricle concha and a rear surface (50%) thereof, as well as the cymba conchae (100%) which is a dominant region of auricle of vagus nerves. These types of stimulators may effectively derive the alpha-waves to undergo a medical treatment to diseases, without being unhandy to carry out it.

The close contact to the ear is performed by the front stimulating portion 204 and the rear stimulating portion 206. The front stimulating portion 204 is provided with a body temperature/blood sugar detecting portion 209 for detecting the body temperature and the blood sugar. Specifically, the body portion 209 has a shape having a gently slant ridgeline, such as a crater, so as to be easily inserted in an external auditory meatus. The body portion 209 has a drilled top surface H to receive an infrared signal.

The front and rear stimulating portions 204 of the left and right stimulating member L and R composing the electric stimulating headphone 20 are provided with a plurality of electric rods 210 and 210', considering a general shape of the ear, i.e., a shape and depth of the concha. The number of electric rods 210 and 210' may be adjusted, if necessary. An end of the respective electric rods 210 and 210' is rounded. Preferably, the length of the respective electric rods is different to each other, in consideration of the depth of the concha. Preferably, the electric rod 210 of the front stimulating member 210 is constructed in such a manner that its length can be adjusted. Preferably, the electric rod 210' of the rear stimulating member 206 is made of a semicircle metal piece.

FIG. 3 is a schematic view depicting a control box of an electric stimulator for alpha-wave derivation according to one preferred embodiment of the present invention. As shown in FIG. 3, the control box includes a battery 116 for supplying an electric power to the entire of the system, a voltage regulating unit 118 for transforming a voltage outputted from the battery 116 to a constant voltage corresponding to one required for the system, and a microprocessor 120 receiving the electric power from the voltage regulating unit 118 for initializing and controlling the system. The microprocessor 120 is provided with an A/D converter (not shown) and a D/A converter (not shown) for processing input and output signals. The microprocessor 120 is connected to the key input supporting key operation of a user. The key input consists of the mode selecting key SET, the up/down control keys UP and DOWN, the auto-mode key AUTO, and the power input key 106. The microprocessor 120 includes an oscillator 122 for carrying out a frequency oscillation wanted by a user, an alarm 124 for alerting whether or not the electric rods 210 and 210' are contacted to user's ears, alerting a perspiring state of the user, or notifying a completion of operation time, a non-contact detector 126 connected to the electric stimulating headphone 20 for detecting the contact state of the electric rods 210 and 210', and a connector 128 connected to the non-contact detector 126 for transferring a corresponding frequency and voltage to the non-contact detector and transferring the contact state of the electric rods 210 and 210' to the non-contact detector 126, according to a control of the microprocessor 120. A D/A converter (not shown) is interposed between the connector 128 and the microprocessor 120. In particular, the D/A converter is built in the microprocessor 120. Displays 102 and LCD are provided to display a frequency, a voltage, a period, an operation time, a contact state, body temperature, blood sugar and the like. Specifically, the frequency and voltage are set in a range of 0 Hz to 100 Hz and 0 mV to 100 mV, respectively, and a corresponding value is displayed. The period is a time interval which the frequency and voltage are applied to the ears, and is displayed as a unit of second. The operation time is displayed as a unit of minute. In addition, an LED is provided to visually notify the use state. The touch state indicating lamp 110, which cooperates with a function of the alarm 124, alerting the completion of the operation time and alerting the contact state of the electric rods 210 and 210' and the wire/wireless mode indicating lamp 108 displaying the state of wire/wireless mode are provided as the LED. The microprocessor 120 includes a transmitter/receiver 130 for transmitting control input data of the user and receiving data of body temperature and blood sugar. The transmitter/receiver is to wirelessly control the control box 10 and the electric stimulating headphone 20.

The electric stimulating headphone 20 connected to the jack 202, which is inserted in the connector 128, for applying the electric stimulation to the ears includes a wire/wireless detector 212 for detecting whether the user does not insert the jack 202 in the connector 128 to operate the electric stimulating headphone in a wireless mode, and a contact terminal 214 connected to the wire/wireless detector 212 to be contacted with the electric rods 210 and 210' contacted to the ears. The contact terminal 214 may be connected to the electric rods 210 and 210', or the contact terminal 214 itself may perform the function of the electric rods 210 and 210'. In addition, in case of operating in the wireless mode, the electric stimulating headphone 20 includes a transmitter/receiver 216 for receiving the signal transmitted to the microprocessor 120 of the control box and transmitting the data of checked body temperature and blood sugar, a remote control unit 218 for controlling the data transmitted from the transmitter/receiver 216, an electric power supply 220 for supplying the electric power to the remote control unit 218 and the contact terminal 214, and an oscillator 222 for oscillating the corresponding frequency to output the corresponding frequency and voltage to the contact terminal 214. The transmitter/receiver 216, the oscillator 222 and the electric power supply 220 operate in the wireless mode only, and do not operate in other situation, i.e., a wire mode.

The non-contact detector 126 detects the contact state of the electric rods 210 and 210'. In the case of the contact state, the present invention performs the control in view of the perspiring state of the user, so as to protect the user and the electric stimulator for alpha-wave derivation.

Specifically, in order to apply the electric stimulation to the auricle perspiring state of the user, the electrode has to be closely attached to the auricle region. According to user's skin conditions, in other words, in the case that the skin becomes moist with perspiration or after taking a shower, an electrical short circuit may happen in the electrodes. The electrical short circuit causes a short-circuit current to flow due to microvoltage applied between the electrodes. Accordingly, an electric power device supplying the electric power to auricle region may be destroyed by the short-circuit current. In addition, the electric stimulation to be applied to the auricle region does not apply to the auricle region of the user, so that the wanted treatment is not performed.

In order to prevent the above short circuit, the non-contact detector firstly detects the contact state depending upon a quantity of electric charge in a capacitor C1. If the electrodes are contacted, in the case where the microprocessor 120 determines that the electric charge is not charged in the capacitor C1 (a low signal generates), the electric power control 132 is activated to supply a direct current through the electrodes of the auricle region. At that time, direct current 200 µA is suitable for the current to be supplied, considering a degree of harmful effects to a body, but the current value may be varied in the range which is not harmful effect to the body, according to an intention of a circuit designer.

A closed circuit is formed by the electrode of the auricle, the electric rods 210 and 210' contacted to the auricle, and a variable resistor R1 connected to the electric rods, and the supplied current flows through the closed circuit. A voltage drop happens in the closed circuit by a degree corresponding to a resultant resistance of a skin resistance of the auricle and the variable resistor R1.

According to the results by the present inventor, the skin resistance between the electric rods 210 and 210' of the auricle region is about 25 to 40 kΩ. For example, if the skin resistance 37 kΩ, the voltage drop of about 0.54 V occurs. In that case, the auricle is in the state capable of performing the treatment, and the value of voltage drop is applied to a voltage comparator COM. If the voltage comparator COM is applied with more than 0.5 volt, the voltage comparator generates a high signal. In the case of a normal state, a voltage of more than set value is applied to the voltage comparator COM, so that an output of the voltage comparator becomes a high state. The electric charge in a capacitor C2 is discharged through a connected transistor TR1 in response to the high signal of the voltage comparator.

At that time, if the capacitor C2 is not charged, the microprocessor 120 regards the auricle as a normal state, interrupts the supply of the direct current through the electric power control 132 (although not shown, a switch or switching circuit selectively supplying the direct voltage and the electric power is built in the electric power control 132, and is operated by the control signal of the microprocessor 120. The operation thereof is widely known in the prior art, and its description will be omitted herein), and supplies a normal waveform through the electrode, thereby performing the treatment. If the user is wet and the auricle is in the electrically connected state, the current supplied to the auricle is only voltage dropped by the variable resistor R1.

Although the present invention utilizes the variable resistor of about 3 to 10 kΩ, it may be changed according to the circuit designer and component characteristics. At that time, the voltage supplied to the voltage comparator COM is less than 0.5 volts, and the voltage comparator COM becomes the low state. The transistor TR is not connected, and the capacitor C2 is charged. The microprocessor 120 regards the auricle as a wet state, and outputs the control signal for turning on/off the contact alarm lamp 110.

Although the present invention describes the basic operation to identify the skin condition of the auricle, the technique for initializing the circuit is widely known in the art, the description of which will be omitted herein. The method of measuring the skin resistance herein is disclosed in Korean Unexamined Utility Model Publication No. 2001-2365 and Korean Unexamined Patent Publication No. 2000-74582, the detailed description of which will be omitted herein. It is intended that the present invention covers alterations of set value and replacements of the circuit device that come within the scope of the claims.

The electric stimulating headphone 20 is provided with the body temperature/blood sugar detecting portion 209. The body temperature/blood sugar detecting portion 209 includes a sensor for detecting an infrared radiation naturally emitted from the human body. Specifically, the sensor is an infrared processing module, in which it can stably measure the skin temperature of a patient by determining the infrared ray emitted from a tympanum, with it being inserted in the external auditory meatus. Since the tympanum uses the same blood vessel as that of a hypothalamus, and is a center of body temperature adjustment, it is a proper position to measure the body temperature. A tympanum thermometer utilizes an ear of a user. The thermometer is inserted in the external auditory meatus, so that the detecting unit is sufficiently enclosed. A lot of radiations reflected from the tympanum transforms the external auditory meatus as a blackbody cavity, of which emissivity is 1. With the above description, the sensor exactly radiates the tympanum and its blood vessel to determine a ratio of the infrared radiation emitted by the patient's tympanum. It is applied to the Plank's law which represents a relationship among a radiation intensity, a spectral distribution and a blackbody's temperature. If the temperature rises, the radiation energy increases, and the radiation energy is varied depending upon a wavelength. A peak value of an amount of radiation is shifted toward a short wavelength according to the temperature rise. Radiation happens over a wide band of wavelength. The entire energy radiated from the blackbody and measured by the non-contact infrared thermometer is the result of the entire energy radiated over every wavelength. This is proportional to integral of the Plank's law to every wavelength. It is fully described in the Stefan-Boltzmann's law of the physics.

In addition, the spectral emissivity of the infrared radiation emitted from the tympanum includes spectra information of tissue, i.e., analyte (i.e., glucose). It may be associated to a concentration of analyte, i.e., blood sugar. Long wavelength infrared energy (i.e., thermal) emitted by a person is monitored, and is used as an infrared energy source to carry out infrared absorption measurement of a specific component of the blood in infrared absorption wavelength characteristics on the components. When a signal ratio is taken in the state that the measurement is synchronized with a cardiac cycle of heart systole and diastole, signal distribution caused by a (not beating) vein or tissue may be cancelled. A temperature sensing unit for measuring an internal temperature of an arm or other vascular organs of a person is utilized to adjust the measurement of component concentration against a temperature depending influence. The infrared processing module is properly depicted in FIG. 4.

FIG. 4 is a perspective view depicting the construction of the infrared processing module. As shown in FIG. 4, an infrared processing module 30 includes a filter portion 31 and an infrared detecting portion 32.

FIG. 5a and 5b are perspective views depicting the construction of the infrared processing module. Referring to FIGS. 5a and 5b, one sensing region 40 is enclosed by a silicon window 41 having a long pass filter, through which only infrared radiation corresponding to the radiation in an internal temperature range of the body is passed. A radiation thermofile detector is a combination of two different metal thermocouples connected in series. An active or hot joint of the detector is melanized to effectively absorb the radiation, while a basis or cold joint is maintained at an ambient temperature of a base 43 of the infrared radiation detecting portion 32. The absorption of the radiation by the melanized region causes the temperature of the hot joint to be increased in proportion to the cold joint. The temperature difference generates a voltage in the detector. The cold joint connected to the base 43 of the infrared detecting portion 32 is thermally coupled to a basis absolute temperature sensor, such as a thermister. A front of the infrared radiation sensing region is covered by a proper infrared bandpass filter 42 having an important spectra characteristic to a radiation line, which is a radiation of a particular wavelength, of the measured analyte. The sensor base 43 or housing attached to the cold joint is thermally contacted to the body such as an external auditory meatus. The infrared radiation emitted by the tympanum radiates upon the hot joint to increase the temperature of the hot joint. The basis 43 having relative high calories and the cold joint thermally contacted to the body are a reference point relative to a point where the infrared radiation spectrally changed due to the concentration variation of the analyte.

As an alternative embodiment of the present invention, the detecting system includes two sensing regions 44 and 45 covered by a silicon window 46 having a long pass filter, through which only infrared radiation corresponding to the radiation in an internal temperature range of the body is passed. A radiation thermofile detector is a combination of two different metal thermocouples connected in series. An active or hot joint of the detector is melanized to effectively absorb the radiation, while a basis or cold joint is maintained at an ambient temperature of a base 43 of the infrared radiation detecting portion 32. The absorption of the radiation by the melanized region causes the temperature of the hot joint to be increased in proportion to the cold joint. The temperature difference generates a voltage in the detector. The cold joint connected to the base 43 of the infrared detecting portion 32 is thermally coupled to a basis absolute temperature sensor, such as a thermister. A front of the infrared radiation sensing region is covered by a proper infrared bandpass filter 42 having a spectrum characteristic to a radiation line of the measured analyte. The sensor base 43 or housing attached to the cold joint is thermally contacted to the body such as an external auditory meatus. The infrared radiation emitted by the tympanum radiates upon the hot joint to increase the temperature of the hot joint. The basis 43 having relative high calories and the cold joint thermally contacted to the body are a reference point relative to a point where the infrared radiation spectrally changed due to the concentration variation of the analyte. One sensing device 44 is covered by a supplementary correlation filter 47, when other sensing region 45 is covered by a proper damping filter 48 having no a spectral band characteristic relative to the measured analyte. For example, the infrared radiation spectrally changed by the tympanum is radiated on one window having the supplementary correlation filter 47 interrupting the radiation emitted by a radiating band of the analyte to be measured and other window passing through a neutral density filter 48 capable of interrupting the same radiation as all wavelengths of an interested range. Therefore, the infrared radiation may be compensated so that it is wholly damped by the supplementary correlation filter of the first sensing region. Two sensing regions 44 and 45 of the infrared detecting portion 32 shown in FIG. 5b are connected to each other so that their outputs can be offset. The infrared radiation is measured by a difference of radiation intensities between two radiation passages in proportion to the concentration of the analyte. The cold joint of two sets of thermofiles connected to the base 49 is thermally contacted to the external auditory meatus of the body, as shown in FIG. 4. Accordingly, the output signal from the infrared detecting portion 32 is stable in no concern with the ambient temperature.

The electric stimulator for alpha-wave derivation according to the present invention will now described.

Embodiment 1

First, the user puts on the electric stimulating phone 20, and pushes down the electric power key 106 to initialize the system. The user sets frequency, voltage, cycle and operation time, respectively, by use of the mode selecting key SET. When selecting the wire/wireless mode, the microprocessor 120 automatically sets the wire/wireless mode according to whether the jack 202 is inserted in the connector 128. Specifically, if the jack 202 is inserted, it proceeds to the wire mode, while if the jack 202 is not inserted, it proceeds to the wireless mode. The mode selection is implemented by the microprocessor 120 according to the voltage value detected by the non-contact detector 126. The control of the applied voltage according to the wet state of the user is similar to the above process, the detailed description of which will be omitted. Since the control of the applied voltage according to the wet state of the user is implemented in the state where the jack 202 is inserted into the connector 128, the control is preferably implemented under the wire mode. The frequency and voltage set by the user are applied to user's ears every set cycle, and the stimulator operates during the set operation time. If the user releases the connection between the jack and the connector 128, the microprocessor 120 determines the release from the connector 128, which is connected to one terminal of the microprocessor 120, to implement the switching of the wireless mode from the wire mode. At the same time, the microprocessor 120 transmits the set value set by the user to the transmitter/receiver 216 of the electric stimulating headphone 20 through the transmitter/receiver 130. When the jack 202 is detached from the connector 128, the wire/wireless detector 212 of the electric stimulating headphone 20 detects the release of the jack 202 and initializes the system. At that time, considering the time required for the initializing process of the electric stimulating headphone 20, the setting data is transmitted from the transmitter/receiver 130. The data received by the transmitter/receiver 216 is read by the remote control unit 218, and the electric power supply 220 outputs the corresponding voltage. The oscillator 222 outputs the corresponding frequency to apply it to a contacting terminal 214. In other words, the electric stimulation is applied to the auricle of vagus nerves to derive 7 Hz to 14 Hz of alpha-waves.

Embodiment 2

A manual mode directly set by the user is described in the first embodiment, while an automatic mode set by the user will be described in the second embodiment.

If the automatic mode is selected by the user, the stimulator operates according to initially set frequency, voltage, cycle and operation time. As the first embodiment, the microprocessor 120 automatically sets the wire/wireless mode according to whether the jack 202 is inserted in the connector 128. It is preferable to use the wire mode of which the jack 202 is inserted, so as to provide the wet state of the user. Even though a wet state of the user cannot be checked, data of body temperature and blood sugar is transferred to the microprocessor 120 through the transmitter/receiver, in the case of the wireless mode. In any case, the stimulator operates according to the value set as an initial value, and the body temperature/blood sugar detector alternatively checks the body temperature and the blood sugar in order. The body temperature and the blood sugar are input to the microprocessor 120 through the jack 202. The microprocessor 120 converts the electric stimulation to the optimum applying state by use of a program itself (which can be set by a manufacturer). At that time, parameter converting it to the optimum state is the body temperature or the blood sugar or a combination thereof, and it is properly shown in FIGS. 6a to 6.

FIG. 6a is a flowchart depicting a stimulating method according to the body temperature, FIG. 6b is a flowchart depicting a stimulating method according to the blood sugar, and FIG. 6c is a flowchart depicting a stimulating method according to the body temperature and the blood sugar.

As shown in FIG. 6a, as the result that the data transmitted from the body temperature/blood sugar detector 209 is analyzed, if the body temperature 'Temp' is less than 36° C. or more than 37.5° C. (step S1), the microprocessor 120 interrupts the application of the voltage to the user (step S2). Then, if the body temperature is less than 36° C. or more than 37.5° C. by again pushing down the automatic mode button or implementing the check of the body temperature by preset times, the electric power is automatically turn off to turn off the system. If the body temperature is not less than 36° C. or not more than 37.5° C., the body temperature is subdivided (steps S3 and S5) to apply the corresponding electric stimulation (steps S4, S6 and S7). The application of stimulation is continuously implemented in the unit of second or is periodically implemented.

As shown in FIG. 6b, as the result that the microprocessor 120 analyzes the data transmitted from the body temperature/blood sugar detector 209, if blood sugar 'BS' is less than 60 mg/de or more than 140 mg/de (step S10), the voltage application to the user is interrupted (step S11). Then, if the blood sugar 'BS' is less than 60 mg/de or more than 140 mg/de by again pushing down the automatic mode button or implementing the check of the blood sugar by preset times, the electric power is automatically turn off to turn off the system. If the blood sugar 'BS' is not less than 60 mg/de or not more than 140 mg/de, the blood sugar is subdivided (steps S12, S14 and S16) to apply the corresponding electric stimulation (steps S13, S15, S17 and S18). The application of stimulation is continuously implemented in the unit of second or is periodically implemented.

As shown in FIG. 6c, when analyzing the data transmitted from the body temperature/blood sugar detector 209, the body temperature/blood sugar detector the body temperature 'Temp' and the blood sugar 'BS' according to the program control of the microprocessor 120 by turns. As shown in the figures, if the blood sugar is less than 60 mg/de or more than 140 mg/de (step S20), the voltage application to the user is interrupted (step S21). Then, if the blood sugar is not less than 60 mg/de or not more than 140 mg/de, the body temperature is detected. If the body temperature is less than 36° C. or more than 37.5° C. (step S22, the microprocessor 120 interrupts the application of the voltage to the user (step S21). Then, if the body temperature is not less than 36° C. or not more than 37.5° C., the microprocessor determines that the body temperature and the blood sugar are a normal state. The control of the voltage application is implemented every body temperature (steps S23 and S31) and every blood sugar (steps S24, S26, S28, S32, S34, S36, S38, S40 and S42). Accordingly, the electric stimulation is applied to the auricle of vagus nerves to derive 7 Hz to 14 Hz of alpha-waves.

FIGS. 7a to 7f are graphs quantitatively showing distribution of alpha waves, beta waves, gamma waves and theta waves before using an electric stimulator for alpha-wave derivation according to the present invention. Referring to FIGS. 7a to 7f, the alpha (α) waves, beta (β) waves, gamma (γ) waves and theta (θ) waves and its distribution are quantitatively depicted, respectively, which are results measured at eighteen regions (ch1 to ch18) of the head. It would be understood from the figures that different distribution is formed every region of head.

FIGS. 8a to 8f are graphs quantitatively showing distribution of alpha waves, beta waves, gamma waves and theta waves after use of the electric stimulator for alpha-wave derivation according to the present invention. It would be understood from the figures that quantitative distribution of the alpha-waves is increased in eighteen regions of the head, respectively, after applying the electric stimulation by use of the electric stimulator.

FIGS. 9a and 9b are views illustrating the state which alpha power is increased in a head before and after use of the electric stimulator for alpha-wave derivation according to the present invention. It would be understood from the figures that eighteen regions of the head are designated and the alpha-waves is increased after applying stimulation.

FIGS. 10a and 10b and FIGS. 11a and 11b are views illustrating the state which synchronization is increased in a forebrain before and after use of the electric stimulator for alpha-wave derivation according to the present invention. It would be understood from the figures that the synchronization of the brain cell related to the respective regions of the brain is increased after applying stimulation by use of the electric stimulation.

The term "synchronization" herein refers to the case where a plurality of nerve cells activate synchronously. For example, a waveform of a low frequency having high amplitude when the eyes close is changed to a waveform of a high frequency having low amplitude when the eyes open, and is again changed to a waveform of a low frequency when the eyes close. Rhythm of the low frequency can be easily seen in the state that a health adult is emotionally stable, with his/her eyes closing. It can be clearly seen in occipital lobes, and the frequency component is 7 Hz to 14 Hz (it average is 10 Hz). Almost same wave (amplitude, frequency, phase) is represented in most of records, and it is called as synchronized EEG.

Accordingly, the increase of the synchronization of the brain cells to the respective regions after applying stimulation is a measure of indicating the fact that the activation of the alpha-waves is increased to ail regions of the brain.

While the present invention has been described and illustrated herein with reference to the preferred embodiments thereof, it will be apparent to those skilled in the art that various modifications and variations can be made therein without departing from the spirit and scope of the invention. Thus, it is intended that the present invention covers all modifications and variations of this invention that come within the scope of the appended claims and their equivalents.

INDUSTRIAL APPLICABILITY

With the above description, the electric stimulator for alpha-wave derivation according to the present invention may treat hypertension, circulatory illnesses, diabetes, adiposity, hyperlipemia, mania and hypochondria, anxiety disorders, memory deficits (i.e., dementia and Alzheimer's diseases), attention deficits, neuropathy encephalopathy, epilepsy, tremor and metal disorders, chronic arthritis and pains, sleep apnea and respiratory disorders, withdrawal symptoms from maternal use of drugs, disorders associated substance abuse, digestive system disorders, growth disorders, menopausal disorders, autoimmune disorders, malignant cancel of organs dominated by vagus nerves, and disorders resulted from hebetation of parasympathetic system (i.e., senescence), according to the applied frequency and voltage.

The invention claimed is:

1. An electric stimulator for alpha-wave derivation comprising:
    a control section including: a key input unit for supporting user operation; a microprocessor for setting a frequency, a voltage, a cycle and an operation time according to a key input signal transferred from the key input unit, for controlling an output of the frequency and voltage according to the set data, for determining whether the outputted frequency and voltage are applied to an ear of a user, for performing a switching of a wire/wireless mode by determining whether a jack is connected to an electric stimulating unit, for outputting a transmitting signal to wirelessly transmit a setting data after a predetermined time, when the wireless mode is switched, and for outputting a turn-on/off signal corresponding to an alarm signal and the turn-on/off signal indicative of a wire/wireless mode control state; a control-side transmitter/receiver for transmitting the setting data according to the transmitting signal and transmitting/receiving input/output data; an oscillator for oscillating at a frequency of 1 Hz to 50 Hz according to a frequency output control; and a connector connected to the jack and connected to the microprocessor for determining the wire/wireless state according to variations of input current value;
    a connecting line connecting the connector with the jack and transferring the frequency and voltage from the jack to the electric stimulating unit; and
    the electric stimulating unit including: a contacting terminal connected to the connecting line and adapted to contact an auricle of vagus nerves of the ear; a wire/wireless detecting unit interposed between the connecting line and the contacting terminal for detecting the wire/wireless mode state according to whether it is connected to the jack or not; a remote control unit for determining the wire/wireless mode state, for controlling operation of the electric stimulating unit itself, in the case of the wireless mode, and for controlling the frequency and voltage according to the set data transmitted from the control-side transmitter/receiver; a transmitter/receiver communicating with the control-side transmitter/receiver for transmitting the input/output data to the remote control unit; an oscillator for supplying the frequency to the remote control unit; and a battery for supplying an electric power to the remote control unit.

2. The electric stimulator for alpha-wave derivation as claimed in claim 1, wherein the oscillator oscillates at 7 Hz to 14 Hz.

3. The electric stimulator for alpha-wave derivation as claimed in claim 1, further comprising a non-contact detector for detecting whether the electric stimulating unit is non-contacted to the ear by use of charge accumulation flowing though the jack of the control unit to output the result to the microprocessor.

4. The electric stimulator for alpha-wave derivation as claimed in claim 3, further comprising, in order to prevent electric short circuit when the contact state based on the signal transmitted from the non-contact detecting unit is determined,
   a variable resistor R1 forming a closed circuit together with the contact terminal for performing a voltage drop according to a resultant resistance value;
   a voltage comparator COM for comparing a voltage generated by the resultant resistance value with a predetermined reference voltage;
   a switch TR1 switched according to the comparison results of the voltage comparator COM;
   a capacitor C2 discharged by the switch TR1 to transmit a signal notifying whether there is normality or not to the microprocessor; and
   an electric power control unit, in which the electric power control unit determines the normality when the capacitor C2 is discharged, and interrupts supply of a direct current, and in which the voltage drop only occurs by the variable resistance R1 when the capacitor C2 is not discharged.

5. The electric stimulator for alpha-wave derivation as claimed in claim 1, wherein the microprocessor further includes an A/D converter and a D/A converter for converting the signal inputted/outputted to/from the electric stimulating unit.

6. The electric stimulator for alpha-wave derivation as claimed in claim 1, wherein the microprocessor further includes a timer operating according to setting data comprising a cycle and operation time.

7. The electric stimulator for alpha-wave derivation as claimed in claim 1, wherein the connecting line has a jack at both ends of the connecting line, the jack detached to the connector and electric stimulating unit.

8. The electric stimulator for alpha-wave derivation as claimed in claim 1, further comprising an alarm for outputting an alerting sound, when an alarm signal is outputted according to the determining result of voltage application to the ear.

9. The electric stimulator for alpha-wave derivation as claimed in claim 1, further comprising a display for displaying a set value according to a key input signal transmitted from the key input unit, and for outputting or lighting an operation state.

10. The electric stimulator for alpha-wave derivation as claimed in claim 1, wherein the electric stimulating unit has a body temperature detecting unit configured to be easily inserted in an external auditory meatus, so as to detect a signal for determining body temperature using an infrared processing module, and the body temperature detecting unit has a drilled top surface to receive an infrared signal.

11. The electric stimulator for alpha-wave derivation as claimed in claim 10, wherein the infrared processing module includes a filtering portion and an infrared detecting portion, in which a sensing region is enclosed by a silicon window having a long pass filter, through which only infrared radiation emitted from the external auditory meatus is passed, and in which a front of the sensing region is enclosed by a proper infrared bandpass filter having a spectrum characteristic to a radiation line, which is a radiation of a particular wavelength, of a measured analyte.

12. The electric stimulator for alpha-wave derivation as claimed in claim 1, wherein the electric stimulating unit has a blood sugar detecting unit configured to be easily inserted in an external auditory meatus, so as to detect a signal for determining blood sugar using an infrared processing module, and the body temperature detecting unit has a drilled top surface to receive an infrared signal.

13. The electric stimulator for alpha-wave derivation as claimed in claim 12, wherein the infrared processing module includes a filtering portion and an infrared detecting portion, in which a sensing region is enclosed by a silicon window having a long pass filter, through which only infrared radiation emitted from the external auditory meatus is passed, and in which a front of the sensing region is enclosed by a proper infrared bandpass filter having a spectrum characteristic to a radiation line, which is a radiation of a particular wavelength, of a measured analyte.

14. The electric stimulator for alpha-wave derivation as claimed in claim 1, wherein the electric stimulating unit has a body temperature/blood sugar detecting unit configured to be easily inserted in an external auditory meatus, so as to detect a signal for determining body temperature and blood sugar using an infrared processing module, and the body temperature detecting unit has a drilled top surface to receive an infrared signal.

15. The electric stimulator for alpha-wave derivation as claimed in claim 14, wherein the infrared processing module includes a filtering portion and an infrared detecting portion, in which a sensing region is enclosed by a silicon window having a long pass filter, through which only infrared radiation emitted from the external auditory meatus is passed, and in which a front of the sensing region is enclosed by a proper infrared bandpass filter having a spectrum characteristic to a radiation line, which is a radiation of a particular wavelength, of a measured analyte.

* * * * *